(12) United States Patent
Rahn et al.

(10) Patent No.: US 7,674,383 B2
(45) Date of Patent: Mar. 9, 2010

(54) METHOD AND APPARATUS FOR PACKING CHROMATOGRAPHY COLUMNS

(75) Inventors: Peter C. Rahn, Richmond, VA (US); Romaine R. Maiefski, Oceanside, CA (US); Tivadar Farkas, Harbor City, CA (US); Emmet E. Welch, Aliso Viejo, CA (US)

(73) Assignee: Phenomenex, Inc., Torrance, CA (US)

( * ) Notice: Subject to any disclaimer, the term of this patent is extended or adjusted under 35 U.S.C. 154(b) by 652 days.

(21) Appl. No.: 11/257,655

(22) Filed: Oct. 25, 2005

(65) Prior Publication Data

US 2007/0090035 A1   Apr. 26, 2007

(51) Int. Cl.
*B01D 15/08* (2006.01)
(52) U.S. Cl. .................................... 210/656
(58) Field of Classification Search ............... 210/656, 210/635, 198.2, 232, 238, 282; 141/12, 80
See application file for complete search history.

(56) References Cited

U.S. PATENT DOCUMENTS

| | | | |
|---|---|---|---|
| 3,440,864 A | 4/1969 | Blume | |
| 3,463,320 A | 8/1969 | Patterson | |
| 3,682,315 A | 8/1972 | Haller | |
| 4,168,147 A | 9/1979 | Acuff | |
| 4,270,421 A | 6/1981 | Robinson et al. | |
| 4,309,286 A | 1/1982 | Lenihan, Jr. et al. | |
| 4,549,584 A * | 10/1985 | Morin et al. | 141/73 |
| 4,597,866 A * | 7/1986 | Couillard | 210/198.2 |
| 4,627,918 A * | 12/1986 | Saxena | 210/656 |
| 4,670,141 A | 6/1987 | Shackelford et al. | |
| 4,732,687 A | 3/1988 | Muller et al. | |
| 4,737,284 A | 4/1988 | Hauke et al. | |
| 4,865,728 A | 9/1989 | Larsson | |
| 4,927,531 A | 5/1990 | Sakamoto et al. | |
| 4,956,298 A | 9/1990 | Diekmann | |
| 5,238,556 A | 8/1993 | Shirkhan | |
| 5,366,621 A | 11/1994 | Bidell et al. | |

(Continued)

FOREIGN PATENT DOCUMENTS

DE   4006351 A1   9/1991

(Continued)

OTHER PUBLICATIONS

PTO Translation 09-0832 of German Patent No. 4,114,766.*

(Continued)

*Primary Examiner*—Ernest G Therkorn
(74) *Attorney, Agent, or Firm*—Stetina Brunda Garred & Brucker; Lowell Anderson

(57) ABSTRACT

A slurry chamber is fastened to and held in coaxial alignment with a chromatography column by a V-band. One end of the column has an end cap and frit. A slurry of fluid and chromatographic media is placed in the column and chamber. A piston is forced through the chamber and into the column by a hydraulic ram to expel the fluid and form a media bed in the column. The slurry chamber is removed, and a split end cap is fastened to the column. A threaded recess in the split end cap receives a split, threaded collet. The collet is tightened until it pushes against the piston with the same force as the ram, at which point the ram is released and the column removed for use.

17 Claims, 13 Drawing Sheets

U.S. PATENT DOCUMENTS

| | | | | |
|---|---|---|---|---|
| 5,462,659 | A * | 10/1995 | Saxena et al. | 210/198.2 |
| 5,601,708 | A * | 2/1997 | Leavesley | 210/198.2 |
| 5,610,322 | A | 3/1997 | Unger et al. | |
| 5,736,036 | A | 4/1998 | Upchurch et al. | |
| 6,001,260 | A * | 12/1999 | Hatch et al. | 210/656 |
| 6,095,202 | A * | 8/2000 | Colon et al. | 141/34 |
| 6,139,733 | A | 10/2000 | Hargro et al. | |
| 6,171,486 | B1 * | 1/2001 | Green et al. | 210/198.2 |
| 6,177,008 | B1 | 1/2001 | Treiber et al. | |
| 6,294,087 | B1 | 9/2001 | Hargro et al. | |
| 6,402,958 | B1 * | 6/2002 | Moran | 210/656 |
| 7,101,477 | B1 * | 9/2006 | Willis et al. | 210/198.2 |
| 2003/0183566 | A1 * | 10/2003 | Laub et al. | 210/198.2 |
| 2003/0194814 | A1 * | 10/2003 | Shalon et al. | 436/161 |
| 2003/0205456 | A1 * | 11/2003 | Jamalabadi et al. | 204/157.43 |
| 2004/0025952 | A1 * | 2/2004 | Cunningham et al. | 138/106 |
| 2005/0224414 | A1 | 10/2005 | Izzo et al. | |

FOREIGN PATENT DOCUMENTS

| | | |
|---|---|---|
| DE | 4114766 A1 | 11/1992 |
| EP | 0476995 A2 | 3/1992 |
| WO | WO 2004/024285 | 3/2004 |

OTHER PUBLICATIONS

PTO Translation 09-0856 of German Patent No. 4,006,351.*
Hilgenga, Klaas. "International Preliminary Report on Patentability." International application No. PCT/US2006/040827. Patent Corporation Treaty. Feb. 27, 2008. 15 pages.
"Document A". International Search Report. 27 pages.

* cited by examiner

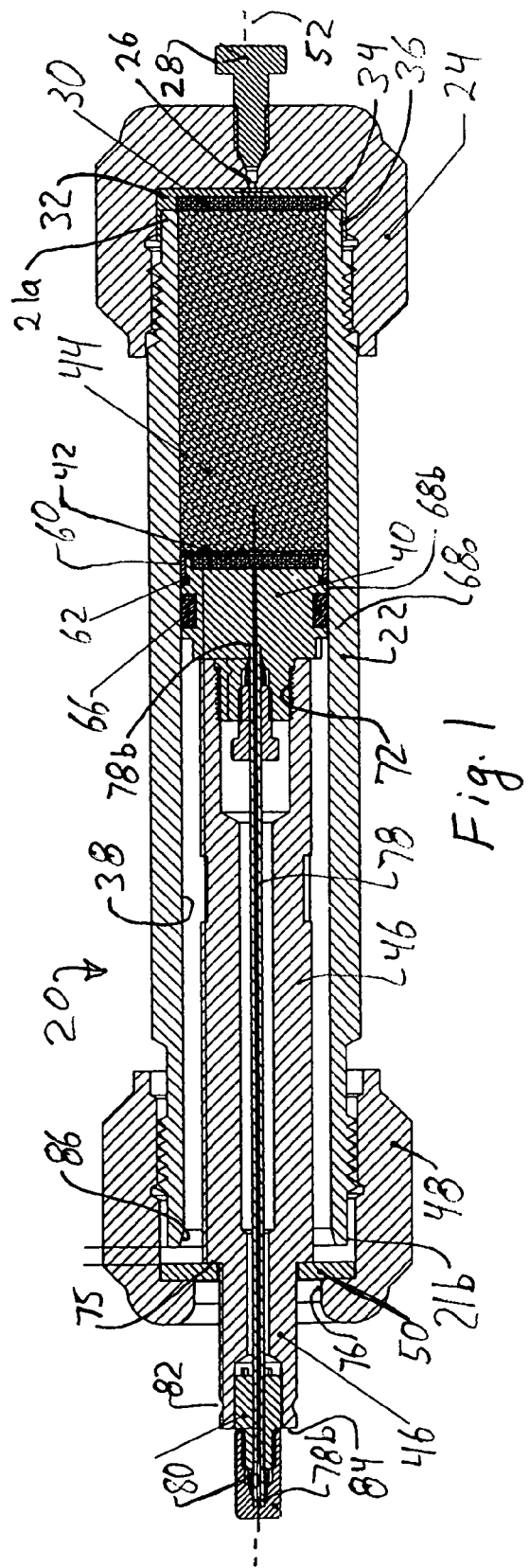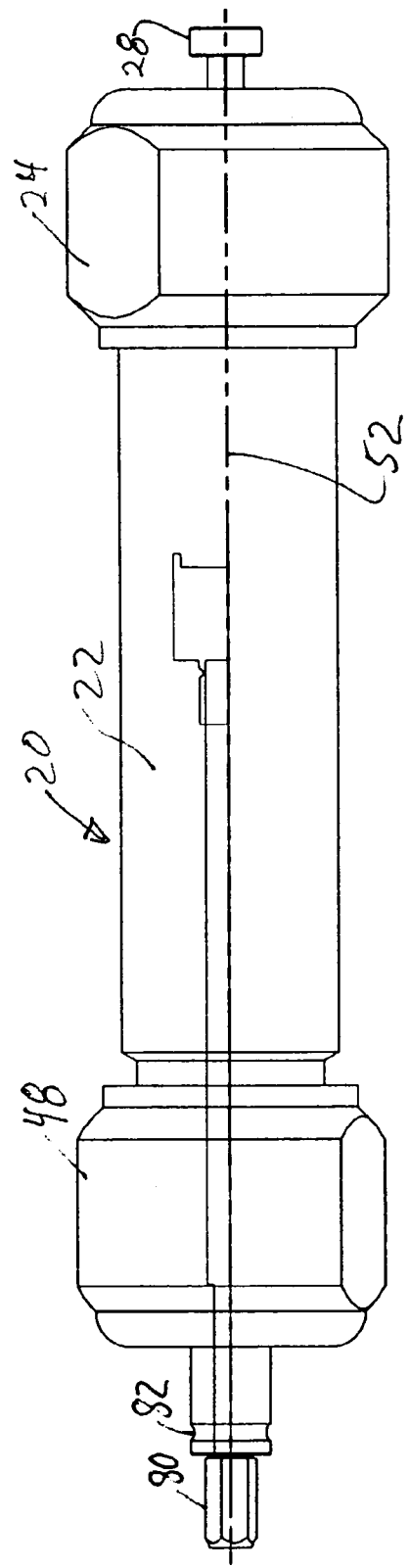

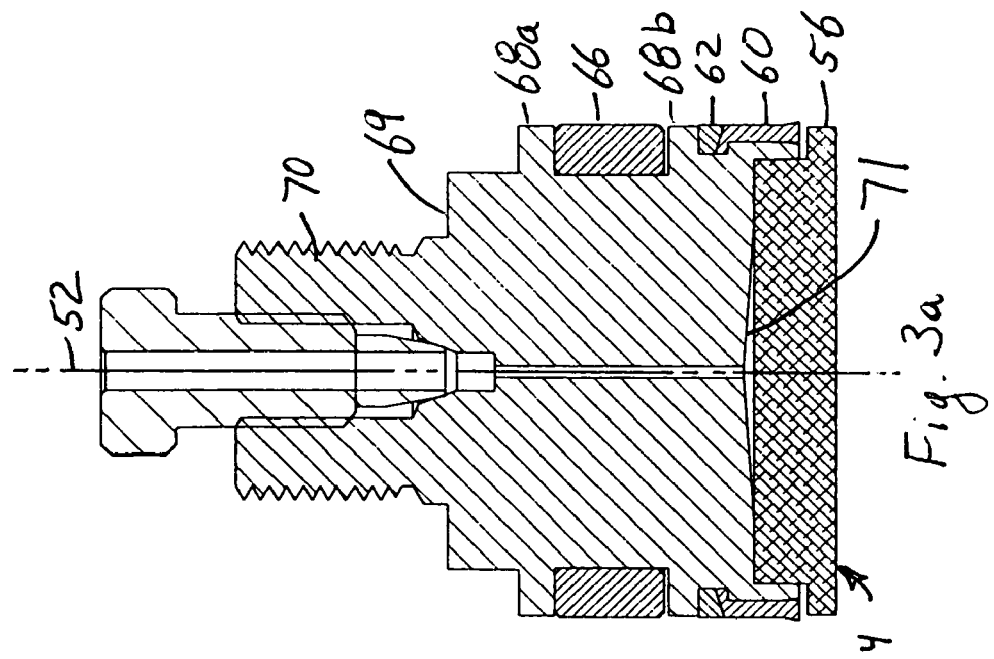
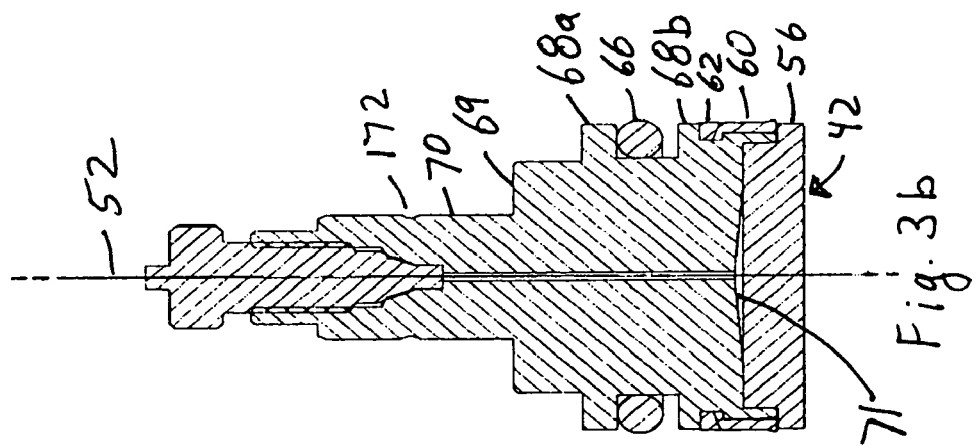
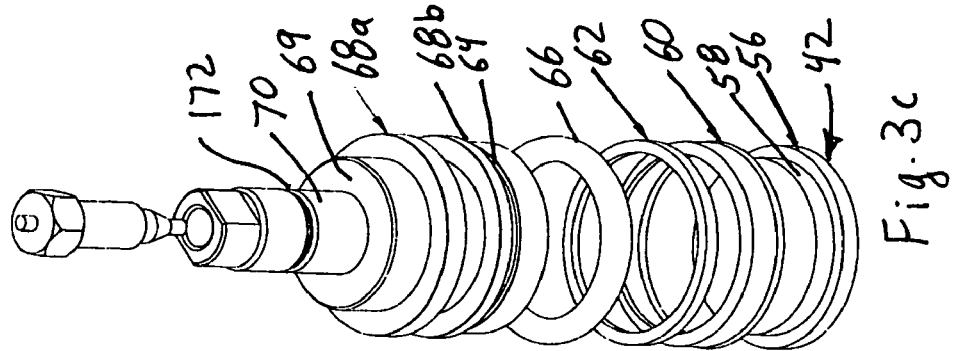

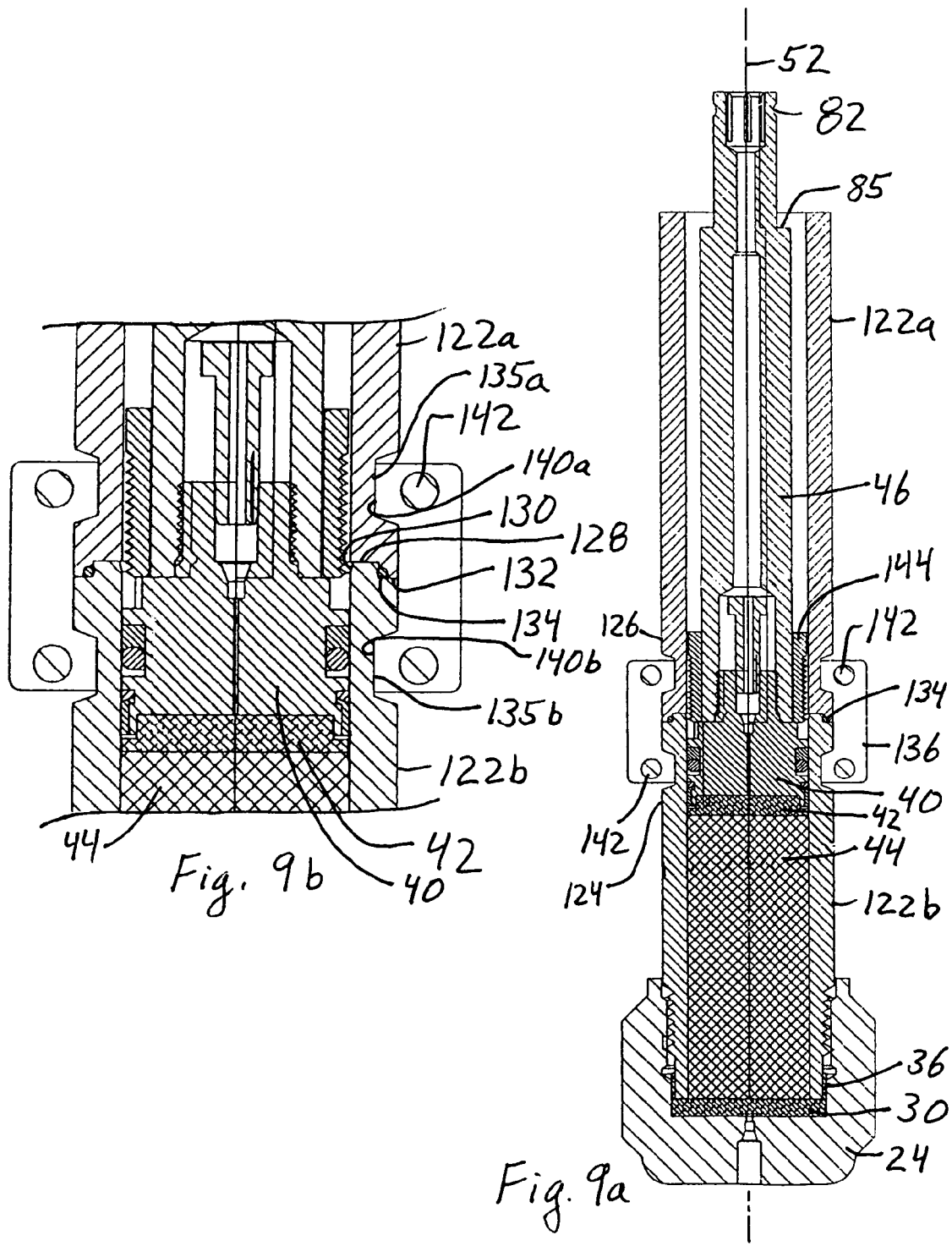

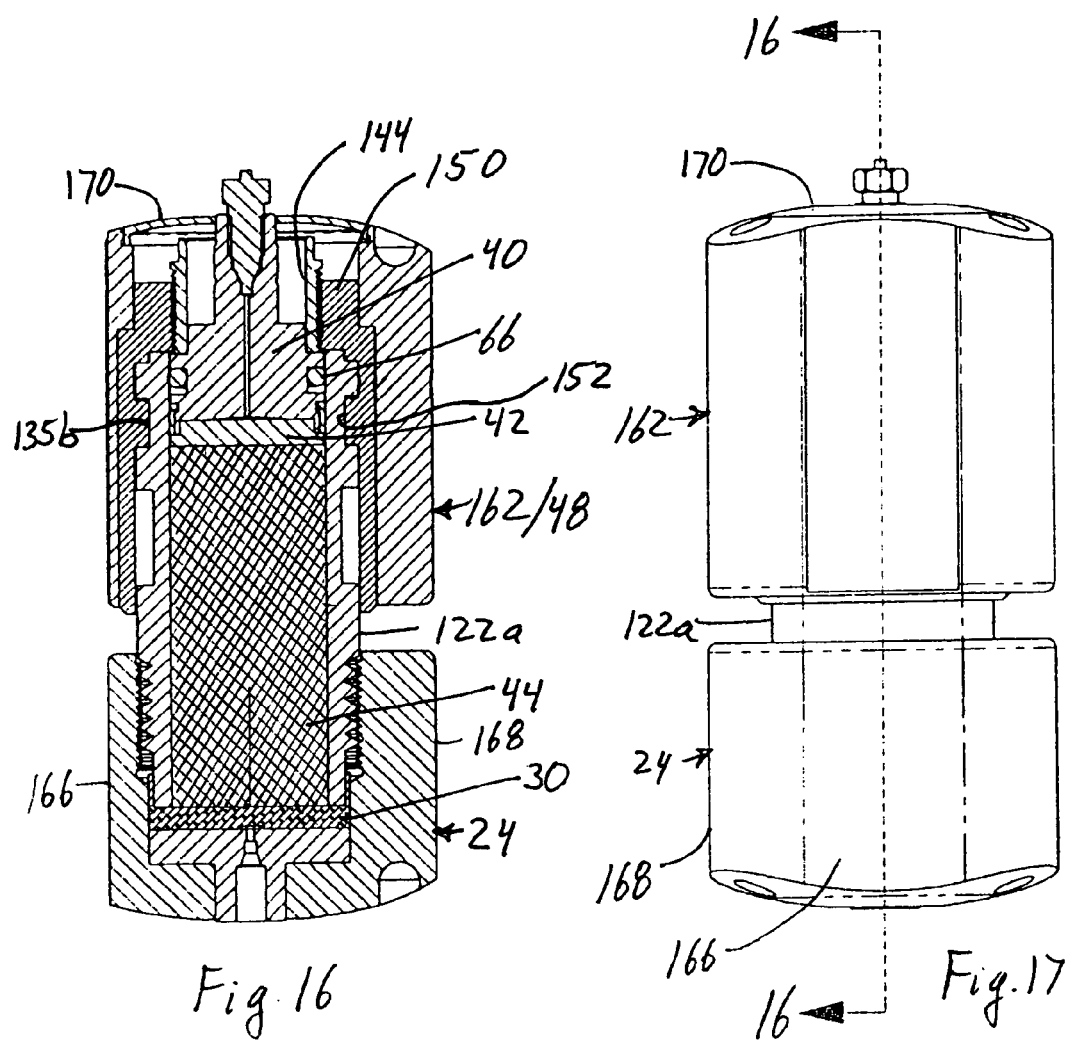

METHOD AND APPARATUS FOR PACKING CHROMATOGRAPHY COLUMNS

BACKGROUND OF THE INVENTION

This application relates to a method apparatus for packing tubular columns with particles, such as packing HPLC columns with media.

Liquid Chromatography is a method for the separation of compounds from a mixture by encouraging a different distribution between the solid particles in the stationary phase of a column and the liquid phase that is passed through the column. The column packing material needs to be well packed and uniformly packed to provide a consistent surface for the separations to occur. Depending on the individual compounds affinity for the column packing material compared to the affinity for the liquid passing through the column determines the difference in time that the compounds reside inside the column. After the compounds exit the column, they are either detected (analytical liquid chromatography) or the compounds are individually collected (preparative liquid chromatography). For the chromatographic separations to be carried out efficiently the column packing material bed must be uniformly and densely dispersed in the column with no channels or voids or stratification of the media that would create re-mixing of the separated compounds.

To achieve this high performance, liquid chromatography columns are generally formed by dispersing or suspending the spherical or irregular chromatographic particles in a suitable solvent creating a slurry. The slurry is placed inside the column tube and the particles are settled to form the column bed by exerting a force onto or through the slurry. This force causes the particles to sediment or "pack" into the column tube. During the packing process, the slurry solvent evacuates through a porous disk called a "frit" which is sufficiently porous to allow liquid to evacuate, but retain the chromatographic particles. As the slurry solvent is evacuated, the chromatographic particles are compressed into a uniform and dense "bed", and the column is then ready for use.

Compressing or packing the column bed is achieved by one of two methods. One common technique of forming chromatographic beds is to produce a slurry inside the column and then using high solvent flow through the column to push the particles towards the outlet of the column. To produce these columns using the slurry technique, the chromatographic column is open at the top during the packing process and this end is attached to one end of a slurry chamber. The chromatographic media slurry fills the slurry chamber and the column tube. The outlet end of the column holds the frit that retains the chromatographic media but permits the liquid to exit the column. The inlet end of the slurry chamber is attached to a high pressure, high volume pump that forces a liquid through the chamber. The high flow liquid forces the particles to migrate towards the exit of the column and the chromatographic media is slowly compressed into a uniform and dense bed.

The slurry technique requires high-pressure pumps to provide the liquid flow until the bed is packed, which may take as long as one hour. This relatively long packing time at high flow significantly increases cost of the final column due to large volume of solvent required, and reduces manufacturing throughput. Once the chromatographic bed is formed, the packed column tube is removed from the slurry chamber and a permanent end fitting is placed onto the column. Another major disadvantage with this high pressure high flow rate slurry packing technique is that the chromatographic media is subjected to very high pressures during the packing process to form the compressed chromatographic bed but this pressure must be released when the column is removed from the slurry chamber. When the pressure is removed from the column, the compacted chromatographic media decompresses or relaxes and the chromatographic bed expands and can move within the column tube. To close the column, the excess media is removed from the top of the column and another frit and end cap is placed onto the column tube to prevent anymore shifting or expansion of the packed bed. The bed shift and subsequent removal of the excess media causes a variable and somewhat reduced bed density, particularly at the head of the column. This variation and reduction in bed density creates performance problems such as settling or voiding of the bed, particularly when the column is operated under high flow rates. This phenomenon is most pronounced on columns that have a relatively low aspect ratio (length/internal diameter) of <25. Currently users in high throughput, high volume preparative applications experience reduced lifetimes with columns prepared using this slurry technique, especially when the column lengths are short due to the lower density beds.

An alternative technique to packing a column is the use of axial compression, as generally described in U.S. Pat. No. 5,893,971. However, most chromatographic columns packed by axial compression are integrated into a single system which includes both the column and the packing apparatus. The column itself is not removable from the system itself, meaning the column is operated as part of the system. Also, the column tube is only partially filled with chromatographic media as most of the tube volume is used as a slurry chamber. Furthermore, as the packing system and column are integrated into a single unit, cost and complexity are also higher.

A newer variation of axial compression packing is described in U.S. Pat. Nos. 5,951,873 and 6,036,755. The column can be removed from the packing system by incorporating a removable spring-rod and piston that maintain active pressure on the column bed. But even this system requires a relatively long column tube, even if the desired bed length may be only ⅓ to ¼ that of the overall column length. The reason for this is that a significant portion of the overall column tube length is required simply to accommodate the uncompressed slurry prior to compression and/or the spring assembly. Thus the design suffers from long and sometime very heavy column assemblies that are inconvenient, impractical and difficult for operators to use in a typical laboratory or purification lab.

These designs are especially impractical in high-throughput purification laboratories where 4-8 columns may be run in parallel, and/or where space is limited. Furthermore, the high cost of the column hardware of this longer and more complex design limits their acceptance in high use or high-throughput environments as they become too costly to operate in large numbers.

Yet another disadvantage of some axial packed columns is that the frit diameter is much smaller than the column diameter. This reduced diameter is due to the space required for a seal or seal assembly that presses against the column wall to prevent leaking of solvent or media when high pressures are applied to the column during axial compression. This reduced diameter leaves an unused area of the column near the outer walls where the frit does not cover the chromatographic bed and the sample is not applied to this area. With short bed columns the distribution of the sample across the entire surface is critical since the bed length is very short and the sample needs to be quickly and uniformly dispensed across the surface. In slurry packed columns the frit diameter is generally equal to or greater than the column diameter.

Therefore, there is a need for more compact, disposable column designs that can be produced by axial compression packing methods and components to improve lifetime and not be cumbersome for the chemist to use.

SUMMARY

A slurry chamber (tube) is fastened to and held in coaxial alignment with a chromatography column by a V-band. One end of the column has an end cap, and frit. A slurry of fluid and chromatographic media is placed in the column and slurry chamber. A piston abuts a stepped diameter frit, with the piston and frit forced through the chamber and into the column by a hydraulic ram to expel the fluid and form a media bed in the column. The slurry chamber is removed, and a split end cap or split retainer are positioned around the column and held in place by a sleeve (1 piece or 2 piece). A threaded recess in the split end cap or split retainer receives a threaded collet. The collet is tightened until it pushes against the piston with the same force as the ram, at which point the ram is released and the column removed for use. The frit preferably has a seal interposed between a smaller diameter of the frit and the adjacent column wall. Likewise, the piston has a stepped diameter, with a seal interposed between a smaller diameter of the piston and the adjacent column wall, with the smaller diameter preferably abutting the frit.

One aspect of the present invention relates to an improved method for the formation of economical and robust liquid chromatography columns by axial compression. Another aspect of this invention relates to a method for removing the slurry chamber while maintaining axial compression on the bed resulting in a column that is compressed but shorter and less complex than traditional axial packed columns while maintaining the flexibility to accommodate bed length variation. A further aspect of this invention significantly reduces the amount of solvent and production time required to pack the column bed compared to the slurry packing technique.

There is advantageously provided a removable slurry/pre-compression chamber. A segmented column or chamber assembly is used that includes a first segment, which is a slurry pre-compression chamber, and a second segment, which is the column chamber. The first segment serves as a slurry and pre-compression chamber to accommodate the chromatographic slurry prior to packing, and during the initial stages of compression. A piston driven by a piston rod or piston sleeve assembly moves the piston towards the fixed end of the column chamber (second segment). The piston itself passes through the first segment and enters the second segment. The piston travels a short distance into the second segment until the media has been adequately compressed to form a stationary bed. The design allows the slurry pre-compression chamber (first segment) to be removed while the piston rod or piston sleeve applies force to the piston to maintain the bed compression. A securing mechanism can then be attached to secure the piston in place, allowing the piston rod to be detached from the piston and removed. The ability to pack by axial compression, and then remove the slurry chamber while keeping the piston in place provides very desirable advantages.

The design also advantageously allows for small variations in final column bed length. A bed compression screw and a V-band clamp design provide fine adjustment of the piston position based on the final bed height achieved when the media is packed into the column. This ability to accommodate variable bed heights ensures that a set compression force can be maintained while accommodating variations (preferably small variations) in the amount of media packed in a column. A variation of up to about one inch (25 mm) in bed height is believed achievable with a given column length.

A two-stepped, hat shaped frit design is also advantageously provided. The frit design increases the amount of the column bed surface area covered by frit allowing quicker dispersion of the sample across the column bed. Older axial compression designs use a piston seal to engage the column wall and the frit was smaller in diameter than the column bed. The older design leaves an area between piston assembly and the wall that was not available for separations. The two-stepped, hat-shaped frit design is very useful for short bed length columns where the sample must be dispersed across the media as quickly as possible. This frit design is also believed to provide advantages for longer length columns.

There is also provided a mechanism and method for maintaining axial compression on the column bed while the slurry chamber is removed and replaced by a bed compression mechanism, such as a screw. Advantageously, the column bed is not allowed to relax or expand after packing. The compacted bed is compressed once during the packing process and this pressure is maintained when the inlet end fitting is attached. This avoids the need for springs to maintain the bed compression.

In one aspect of this invention there is provided a portable tubular chromatography column having a tubular body with an inner diameter with first and second ends covered by first and second end caps, respectively. The column has a bed of chromatographic media placed between a first and second frit all located inside the body. A piston abuts the first frit and exerts a predetermined pressure on the bed. An adjustable locking mechanism has a support fastened to the body and has a threaded adjuster interposed between the support and the piston such that rotation of the threaded adjuster increases or decreases the force the piston exerts on the bed.

In a further variation of this above described embodiment the support clamps to an exterior of the body, and preferably forms a V-band clamp. Further, the threaded adjuster optionally comprises a collet having one end abutting the piston. Advantageously, the collet has multiple lead threads, with two leads being preferred. In a further variation the support comprises a split end cap that is clamped to the body. The split end cap can optionally enclose one end of the tube or chamber and is optionally held together by an encircling structure. Preferably the split end cap has a threaded recess therein to receive the adjustable fastener. The recess also preferably has multiple lead threads. Further, the collet preferably has a wrenching surface.

In further variations, the frit extends to adjacent the inner diameter of the column body with no seal interposed between the frit and the column wall. The frit preferably has a first diameter about the same as but slightly smaller than the inner wall with no seal interposed between the frit and the inner wall. Advantageously, the frit has first and second concentric diameters with the diameter of the frit abutting the media being the first diameter and being larger than the second diameter. The piston preferably has at least one seal interposed between the piston and the inner wall with at least one seal selected to provide a seal at fluid pressures of several thousand psi. Moreover, a portion of the piston preferably extends outside an end of the tubular body.

In a further aspect of this invention, a new frit is provided. The frit is preferably, but optionally for use with a chromatography column having a tubular body with a cylindrical interior having a first diameter. The frit has a first cylindrical portion having a diameter about the same as but slightly smaller than the first diameter of the column. The frit has a second cylindrical portion having a smaller diameter, with the first and second portions being concentric. In further variations the frit is integrally and unitarily formed from a single piece of material, or alternatively the frit is formed from two abutting frits of different diameter.

In a further aspect of this invention there is provided a method for packing a tubular chromatographic column having a first and second opposing ends defining a first length and having an end cap on the first end of the column. The column has an interior diameter. The method includes abutting a slurry chamber to the second end of the column and coaxially with the column and forming a fluid tight seal between the slurry chamber and the second end of the column. A slurry is placed in the column tube and slurry chamber, with the slurry containing fluid and chromatographic media. A piston is placed in the slurry chamber, with the piston having seals interposed between the piston and the slurry chamber and a frit interposed between the piston and the slurry. The piston is advanced through the slurry chamber and at least part way into the column. Advancement of the piston is stopped when the media in the slurry forms a bed that is compacted to a desired pressure or length.

In a preferred form, the method includes locking the piston to the column. More preferably the method includes removing the slurry chamber and locking the piston to the column without releasing the pressure on the bed. Advantageously, the frit comprises a stepped disk having first and second concentric and different diameters with a larger diameter abutting the slurry. More preferably, a seal is interposed between the smaller diameter and the inner diameter of the column and no seal is interposed between the larger diameter and the inner diameter of the column. Further, a chamfer is preferably formed on an interior edge of the second end of the column, although the chamfer is optional and can especially be omitted if the mating parts are sufficiently concentric.

In a further preferred variation, the method includes removing the slurry chamber while maintaining the position of the piston and placing two parts of a split end cap over the second end of the column, where the end caps each have a portion of a threaded recess formed therein. A split, threaded collet or split piston retaining ring with a threaded recess is fastened to the second end of the column. An outside collar is placed over the piston retaining ring and fastened in place. Finally, the threaded collet is advanced in the recess until the collet holds the piston in place.

In a preferably variation on this later preferred method, advancing the piston comprises placing a hydraulic ram in contact with a shoulder on the piston and advancing the hydraulic ram. The slurry chamber can be removed from the column with the ram in place, after which the piston is locked in place, with the ram position being maintained until the slurry chamber is removed from contact with the column and until the piston is locked in place. After completion of packing and locking the piston in place, the column is removed from the ram, and the outlet in the first and second ends of the column are plugged. In further variations of the above methods, forming the fluid tight seal includes placing a V-band clamp over the juncture of the slurry chamber and the column. The locking step also can include placing a V-band clamp around the second end of the column.

In a further aspect of this invention, a multiple segment chromatography assembly is provided. The assembly includes a slurry chamber having a first and second open end, the chamber having walls defining an inner cylinder of diameter D, and a chromatography column having an first and second opposing ends and an end cap over the second end. The second end of the slurry chamber abuts the first end of the column. The column has walls defining an inner cylinder of diameter D. An annular seal is placed in a recess formed in part in an exterior surface of the first end of the column and formed in part by an exterior surface of the second end of the chamber. A V-band clamp encircles the seal and cooperates with at least one of recesses or protrusions in the exterior of the chamber and column to hold the chamber and column in coaxial alignment.

In further variations of this apparatus a chamfer is formed on an interior edge of the first end of the column. Preferably a chamfer is also formed on an interior edge of the first end of the slurry chamber. A slurry of fluid and chromatographic media is placed in the chamber and column. A piston is placed in one of the chamber or column. The piston has at least one seal interposed between the piston and the cylindrical wall of the chamber or column in which the piston is located. Preferably, the piston extends at least part way into the column and the piston has a frit with a first diameter about diameter D and having a second, smaller diameter.

BRIEF DESCRIPTION OF THE DRAWINGS

These and other advantages and features of the invention will be better appreciated in view of the following drawings and descriptions in which like numbers refer to like parts throughout, and in which:

FIG. 1 is a sectional view taken along 1-1 of FIG. 2;

FIG. 2 is a plan side view of a chromatography column;

FIG. 3a is a cross sectional view of one embodiment of a piston and frit;

FIG. 3b is a cross-sectional view of a second embodiment of a piston and frit show in the piston and frit of FIG. 1;

FIG. 3c is an exploded perspective view showing a piston and frit of FIGS. 1 and 3b;

FIGS. 9a and 9b are a sectional view and an enlarged portion of that sectional view showing column and slurry chamber of FIGS. 7-8 held by a V-band;

FIG. 11 is sectional view showing the configuration of a column of FIGS. 7 and 9 held in a recessed support plate before the packing of the column;

FIG. 14a is a plan view of a further embodiment of a packed column;

FIG. 14b is a sectional view taken along 14b-14b of FIG. 14a;

FIG. 16 is a sectional view taken along 16-17 of FIG. 17;

FIG. 17 is a side plan view of the column of FIG. 15; and

DETAILED DESCRIPTION

Figure 4:
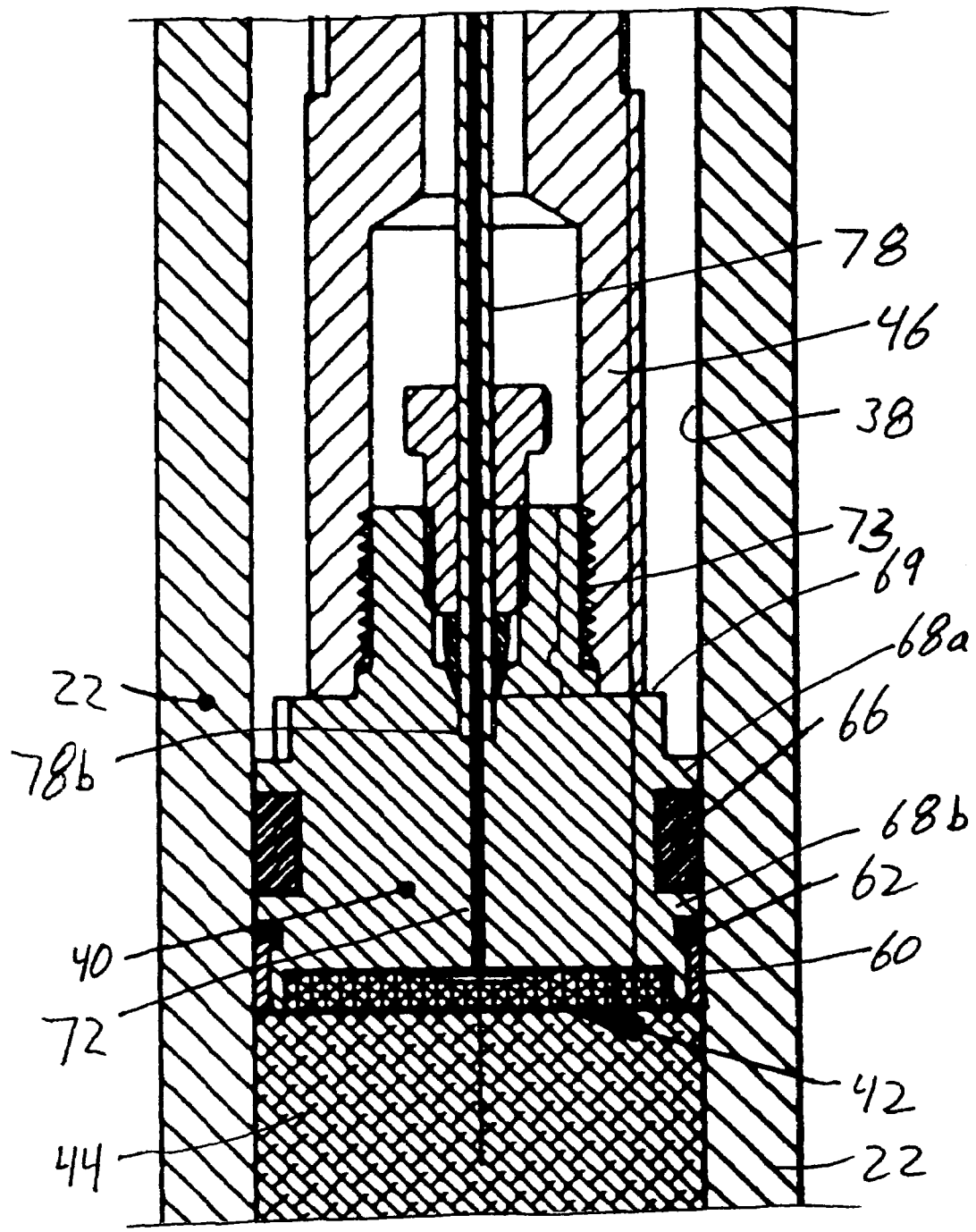
FIG. 4 is a partial sectional view illustrating the piston of FIG. 3b in a packed column.

Two primary embodiments are shown, with the first embodiment using a single-piece, longer body and the second embodiment using a two-piece, segmented body.

Referring to FIGS. 1-4, a chromatography column 20 is provided having a tubular body 22 that is preferably cylindrical and has opposing ends 21a, 21b. A downstream end cap 24 is fastened over a first, downstream end 21a, preferably the downstream or outlet end. The end cap 24 preferably, but optionally, is cup-shaped and has a generally flat end with a tubular skirt having interior threads that mate with exterior threads on the outside of the body 22 to fasten the end cap 24 to the body. An outlet 26 is formed in the generally flat end of the cap 24 and a threaded plug 28 engages mating threads on the outlet passage to releasably block the outlet 26.

A first frit 30 is placed in or over the first end 21a and held in place by the first end cap 24. A cup-shaped frit holder 32 is preferably, but optionally interposed between the first frit 30 and the first end cap 24. The frit holder 32 has a generally flat end with a two-stepped skirt forming a first, smaller diameter recess 34 into which the frit nests during use, and forming a second, larger diameter recess 36 which receives a stepped end 21a of the body 22. A lip on the distal portion of end 21a abuts a shoulder formed between the different diameters of the recesses 34, 36 to form a seal, with the larger diameter recess 36 overlapping the stepped end 21a to form a further seal. The end cap 24 holds the frit holder 32 and frit 30 in place and in sealing engagement with the first end 21a of body 22. The frit holder 32 has an outlet aligned with outlet 26.

The interior of the tubular body 22 preferably has a cylindrical cavity 38 within which slides a piston 38 has a downstream end that preferably, but optionally, abuts a second frit 42. Between the frits 30, 42 is a media 44 typically forming a stationary phase for chromatographic analysis. The media typically comprises silica or polymer particles coated with various chemicals suitable for chromatographic analysis.

The piston 40 is urged against the frit 42 and media 44 by piston sleeve 46 that in turn is held in place by second end cap 48 and thrust washer 50 as described in more detail below. The column 20 has a longitudinal axis 52 that preferably extends through the center of the piston 40. As used herein, the downstream end or direction refers to a direction along axis 52 as used during packing, and in the illustrated embodiments that direction is from the end cap 48 toward the end cap 24, and the upstream direction is opposite thereto. In actual use the mobile phase preferably passes in the same direction, but it can pass through the column in either direction so upstream and downstream could be reversed during actual use.

Referring to FIGS. 1 and 3b-3c, the piston 40 and second frit 42 are described. The downstream end of piston 40 has a wall 54 extending downstream toward the downstream end cap 24 and along the longitudinal axis 48. The wall 54 forms a cylindrical recess sized to receive a portion of frit 42. The frit 42 is generally hat-shaped having a first disk shaped portion forming flange 56 with a circular periphery slightly smaller than the inner diameter of the walls 38, preferably about 0.001 inches smaller in diameter. The disk-shaped flange 56 extends radially outward from the axis 48 beyond a smaller diameter cylindrical boss 58 located on the upstream side of the flange 56. The frit 42 thus comprises the flange 56 and boss 58, which are preferably formed with internal passageways to distribute fluid evenly across the downstream face of flange 56.

The recess formed by wall 54 on the piston 40 receives the cylindrical boss 58, with the downstream end of the wall 54 preferably abutting the flange 56 of the frit 42.

A first seal 60 is preferably, but optionally interposed between the exterior of the wall 54 and the adjacent inner wall 38 of the body 22. The first seal 60 advantageously has a rectangular cross-section with its longer dimension along the longitudinal axis 52 and with a downstream end of the seal 60 preferably abutting the flange 56. The first seal 56 is preferably an elastomer or polymer such as polyethylene or polypropylene or polytetrafluoroethylene or rubber. A St. Gobain #450151883 seal is believed suitable. The first seal helps restrict media 44 and liquid from passing between the piston 42 and inner wall 38.

An optional second seal 62 abuts the upstream end of the first seal 60. The second seal 62 is preferably an elastomer seal, located in a corresponding groove 64 in the piston 40. The second seal 62 is preferably an elastomer or polymer such as polyethylene or polypropylene or polytetrafluoroethylene or rubber. The second seal 62 could be an O-ring seal. The second seal 62 helps keep the first seal 60 from moving upstream along axis 52. It may also optionally help seal against media 44 and liquid passing between the piston 40 and inner wall 38.

A wear ring 66 is located between two axially spaced flanges 68a, 68b on piston 40. The ring 66 also optionally provides a further sealing surface. The flanges 68a, 68b extend radially outward from axis 52 to form a circular periphery slightly smaller than the inner diameter of interior wall 38. The wear ring 66 preferably has a rectangular cross section, and has an axial length abutting the inner wall 38 sufficient to reduce rocking of the piston within the cylindrical wall 38 as the piston 40 moves along the axis 52. Wear ring 66 could be polyethylene or polypropylene or polytetrafluorethylene. It could have an O-ring configuration, or other configurations.

A shoulder 69 is formed on the upstream end of the piston 40 with an upstream boss 70 of smaller dimension extending upstream. The shoulder 69 is preferably a continuous annular surface facing upstream but intermittent surfaces could be used. The boss 70 preferably has a cylindrical exterior with threads thereon. A fluid passage 72 extends through the piston 40, preferably coincident with axis 52. The fluid passage 72 has a downstream end in fluid communication with frit 42, and preferably opens onto boss 58 of frit 42.

The wall 54 forms a recess having a top or upstream surface 71 that is generally orthogonal to the longitudinal axis 52. Preferably, however, as seen in the figure, the surface 71 is slightly inclined upstream and toward the longitudinal axis to form a shallow conical recess between the surface 71 and the adjacent frit 42. This conical space avoids clogging in the event the sample contains some particulates, and it also helps spread the sample over the frit. An inclination angle of about 3° is believed suitable to form this conical space.

The piston sleeve 46 preferably comprises a tubular shaft having a downstream end configured to abut shoulder 69, with an interior sized to fit over the boss 70. Preferably, but optionally, the interior on the downstream end of the piston sleeve 46 is threaded and configured to threadingly engage threads on boss 70. A shoulder 75 on an upstream portion of piston sleeve 46 abuts one of the end cap 48 or the thrust washer 50. The thrust washer 50 is preferably a relatively thick stainless steel in order to maintain the position of the piston accurately. The piston sleeve 46 preferably extends through an opening 76 in the end portion of upstream end cap 48. A tube 78 extends through the piston sleeve 46, preferably coincident with axis 52. An upstream end 78a of the tube 78 is adapted to be placed in fluid communication with chromatography equipment to introduce a mobile phase into the column 20. A downstream end 78b of the tube 78 is configured to fasten to be placed in fluid communication with the upstream end of piston 40 and its fluid passage 72. A cap 80 blocks the inlet end 78a.

A detent 82 is placed adjacent the upstream end of the piston sleeve 46. A circular recess extending around the outer periphery of the piston sleeve 46 is believed suitable to form detent 82. The upstream end of the piston sleeve 46 forms a driving surface 84, or if desired an additional driving shoulder is formed on the piston sleeve 46 facing upstream to serve the purpose of the driving surface 84 as described later. The locking surface 75 is formed in the sleeve 46. Preferably the locking surface 75 takes the form of a shoulder on the sleeve, and more preferably comprises an annular shoulder rather than intermittent surfaces.

The upstream end 21a of the body 22 is preferably formed with a chamfer 86 on the inside of the body 22 and angled outward from longitudinal axis 52. The chamfer 86 extends to the flattened or rounded lip of the body 22 which faces upstream.

Figure 5:
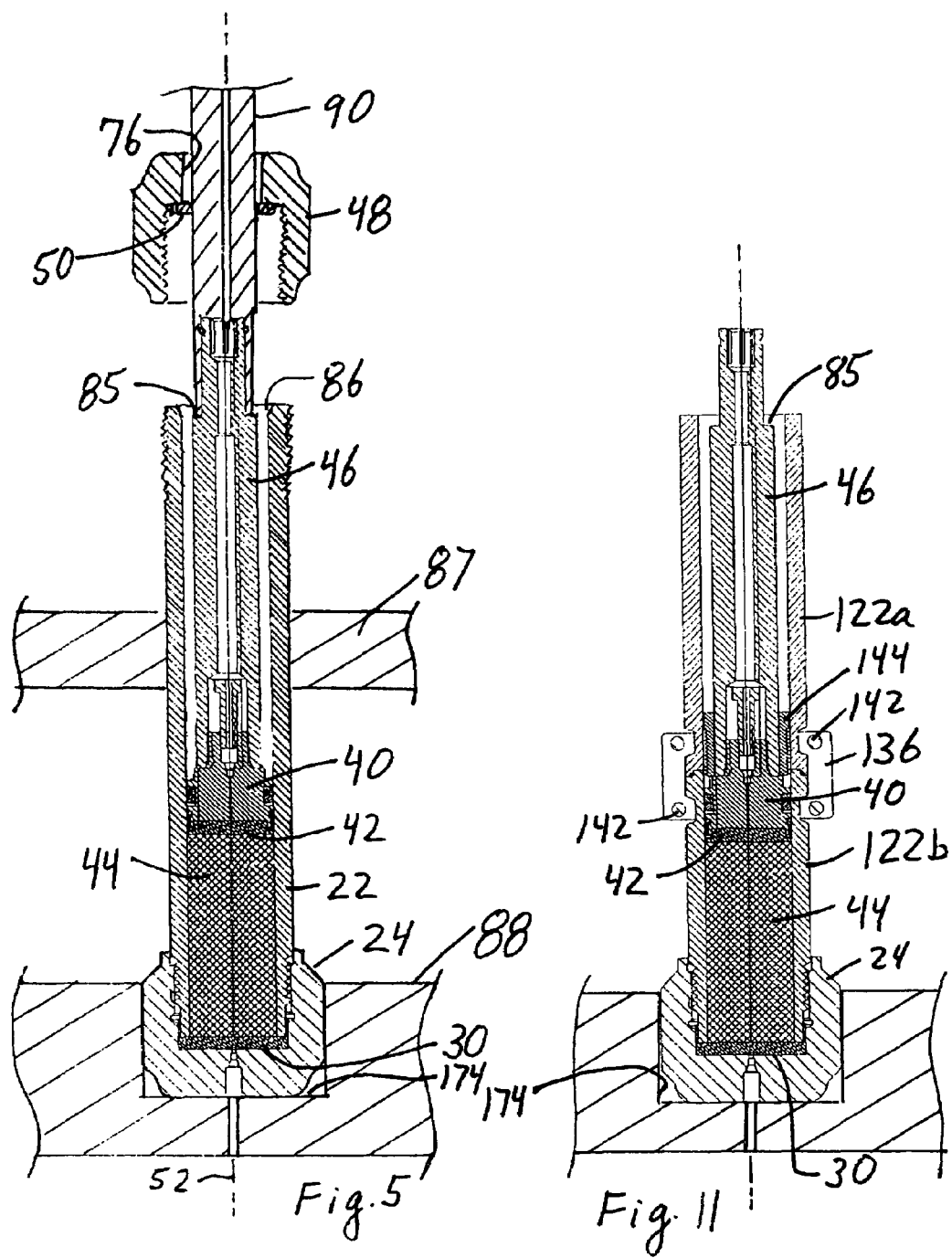
FIG. 5 is a sectional view showing the configuration of a column of FIG. 1 held in a chuck and a recessed support plate before the packing of the column.

Referring to FIGS. 1 and 5, the packing of the column 20 is described. The downstream end cap 24 is placed on body 20 to hold the downstream frit 30 in place. The column 20 is placed in a holder with the upstream end 21a being open rather than covered. Preferably, but optionally, the column 20 is placed in a chuck 87 which is tightened to abut the body 22 and hold the column so the centerline 52 aligns with the centerline of the chuck. A three part chuck 87 is preferred. The downstream end of cap 24 can abut a support surface 88 as shown, or the chuck 87 can grip the body 22 sufficiently for the following packing.

A predetermined amount of media 44 is placed in a beaker and mixed with a fluid to form a slurry. The slurry is preferably sonicated to remove air and further mix the media 44 and fluid. The slurry is then poured into the inside of the body 22. The flask is rinsed with the fluid, preferably twice, and the fluid poured into the body 22 in order to ensure all the media is placed into the body 22. Additional fluid is added, if needed to fill the fluid level to the chamfer 86. It is undesirable to force air through the column, so the fluid level is high enough to avoid air entrapment or a release valve is provided. Alternatively, the slurry could be pumped from a tube or other filling methods could be used. The outlet passage 26 is preferably not blocked at this stage so fluid can exit through the outlet 26 under the force of gravity.

The piston 40 is placed onto the piston sleeve 46 so the end of the sleeve abuts the piston shoulder 69. Preferably mating threads on boss 70 engage mating threads on the inside of sleeve 46 to form a threaded engagement that prevents relative axial movement of the sleeve and piston. Advantageously a metal cap is placed over the end of sleeve 46 to block fluid flow out of the upstream end 78a of tube 78. The hat-shaped frit 42 is placed in the piston, and the upstream end cap 48 and thrust washer 50 are placed on the piston sleeve 46. As desired, a locking mechanism can also be placed over the piston sleeve 46.

The piston sleeve 46 is placed into a press 90. The press 90 preferably, but optionally comprises a hydraulic ram and will be described as such. The detent 82 can engage a mating releasable detent pin in the press 90 to hold the piston sleeve 46 in place, along with any locking mechanism and piston 40 attached to the sleeve. The piston sleeve 46 is positioned in the ram 90 such that the longitudinal axis of the sleeve coincides with the longitudinal axis 52 of the body 22.

The ram 90 then advances the piston into open end of the body 22, with the chamfer 86 helping to guide the mating parts and accommodate slight misalignments. Preferably a slight amount of excess fluid is forced over the chamfered lip 86 in order to ensure no air is entrapped between the frit 42 and the fluid. The advancement of the ram 90 and piston 40 is slow during this initial engagement portion. The ram 90 advances the piston 40 into the body 22 until the wear ring 66 abuts the interior wall 38 at which point the speed of the ram can increase if desired. The advancing piston 40 forces fluid out the outlet passage 26 while the frit 30 retains the media inside the body 22. When the fluid is largely expelled from the body 22 the piston 40 compresses the media 44 at which point the pressure rapidly increases.

The ram 90 advances the piston 40 until a desired pressure is reached at which point movement of the piston 40 is halted. At that point the fluid is largely pressed out through passage 26 and the media 44 is compacted to form a stationary phase for a desired use, preferably for chromatographic analysis. The relative movement of the piston 40 and shaft 46 relative to the body 22 is then fixed. This is preferably, but optionally achieved by moving thrust washer 50 until it abuts locking shoulder 75, or if no thrust washer is used, the cap 48 is advanced until a portion of the cap abuts the locking surface 75. Preferably, but optionally, the locking shoulder 75 extends adjacent the opening 76 in the cap 48, so that the thrust washer 50 does not have a significant unsupported or free length extending between the cap 58 and the shoulder 75. The cap 48 has interior threads engaging mating threads on the outside upstream end of the body 22. The length of the sleeve 46 and location of the locking shoulder 75 are selected relative to the length of body 22 and location of these mating threads so that the threads can urge and thrust washer 50 along axis 52 to abut the locking surface 75.

The cap 48 is tightened until it causes thrust washer 50 to push against shoulder 75 and sleeve 46 to further compact media 44. A linear movement gauge 92 in communication with the ram 90 shows a slight increase in piston movement. The linear movements 92 can preferably, but optionally, read movement to the second or third decimal point. When the media 44 is further compacted a slight amount of 0.01 or 0.001 or preferably 0.0001 on the linear movement gauge, then the ram 90 is released and the cap 48, thrust washer and locking surface 75 hold the sleeve 46 and piston 40 in place. The column 20 is removed from the chuck 87. The plug 28 blocks the outlet passage 26. The metal cap on the upstream end 78a is removed if desired, and replaced with a plastic cap and/or union. The packed cartridge is then suitable for shipping and/or use. A force gauge could also be used instead of or in addition to a linear movement gauge.

Figure 6:
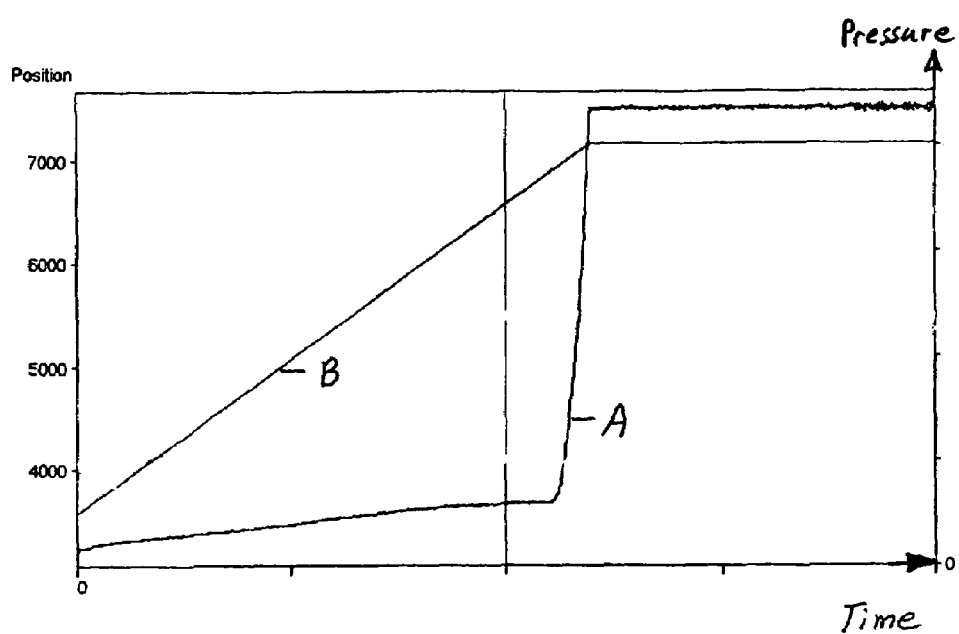
FIG. 6 is a graph showing how pressure on a bed of media increases as it is dynamically and hydraulically packed using the column of FIGS. 1 and 9.
Figure 8:
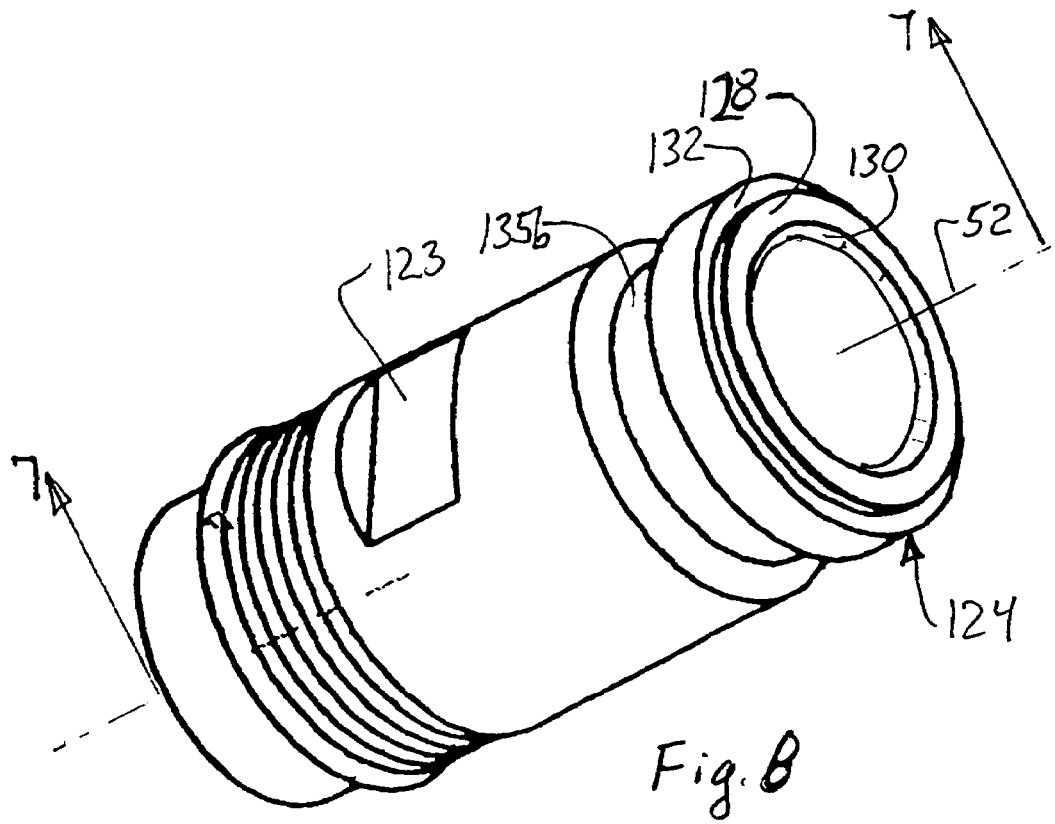
FIG. 8 is a perspective view of a column of a further embodiment.
Figure 7:
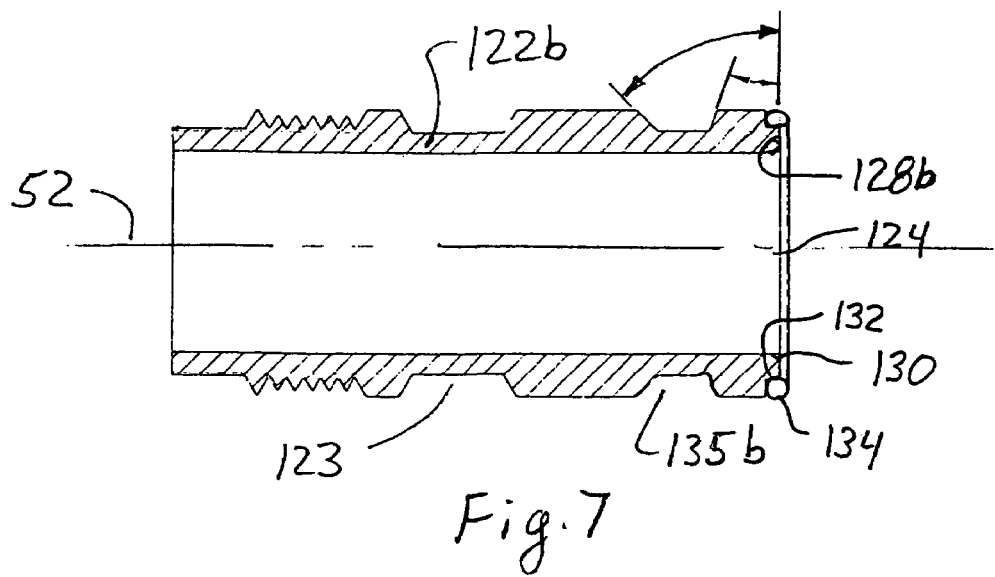
FIG. 7 is a sectional view taken along 7-7 of FIG. 8.

Referring to FIG. 6, an illustrative graph of the pressure exerted by ram 90 on the left vertical graph, versus the position of piston 40 shown on the horizontal graph. The piston movement is represented in time. As the piston 40 expels the excess fluid from the body 22 and outlet 26, the pressure on ram 90 increases fairly linearly as the media 44 is compacted and the fluid being forced through the bed experiences increased flow resistance. When the fluid is largely expelled through outlet 26 the pressure increases significantly as further motion of the piston 40 compacts the media 44 in the remaining fluid. If the pressure increase too much the media 40 will deform or it will crush and form fines, each of which decreases flow through the media bed 44. The desired compaction pressure will vary with the particular media being used. The movement of piston 40 is stopped when the pressure reaches a desired pressure.

This first embodiment achieves a uniform hydraulic packing of the media 44 by piston 40 which is desirable for uniform flow of mobile phases passing through the stationary bed formed by the compacted media 44. But this embodiment requires a long body 22 and a long sleeve 46 which make the end column heavy, and which requires more material than desired. The body 22, sleeve, end caps 24, 48 are made of metal, typically stainless steel, and that material is not only heavy, but expensive. It is thus desirable to reduce the length of body 22 and eliminate, if possible, piston sleeve 46.

Referring to FIGS. 7-10, a second embodiment is described which uses the same piston 40 described above, but which uses a segmented body 122. For parts that are not changed the part numbers are not altered and are the description is not repeated.

The body 122 is formed of two parts, a removable, upstream tube 122a and a remaining downstream tube 122b. Both parts 122a, 122b are used for packing while removable tube 122a is removed for use, as described later in more detail. The upstream tube 122a forms a slurry chamber, while the downstream tube 122b forms the column. Tubes 122a, 122b are releasably joined by a removable, V-Band clamp. An optional wrenching surface 133 can be provided on the outside of body 122.

The slurry tube 122b has a length sufficient to hold the desired slurry media 44 prior to the media being packed. Preferably, but optionally, the length is also sufficient to accommodate at least a portion of piston 40. The upstream end 124 of column 122b is configured to seal against the downstream end 126 of slurry chamber 122a. The seal is designed to withstand the hydraulic packing pressures, which typically range from 2000-6000 psi, but which can be larger or smaller depending on the particular column and media. The seal is preferably a face seal between the abutting faces of the bodies 122a, 122b. But the seal could be an axial seal extending along the length of longitudinal axis 52, or it could be both a face seal and an axial seal.

One illustrated seal is described. The mating ends of bodies 122a, 122b each have a wall 128a, 128b on the inside of the tubular body 122a, 122b extending parallel to axis 52. Each wall 128a, 128b forms a short cylinder. Each wall 128a, 128b also forms a recess 132a, 132b on the exterior of the wall. When the ends of the walls 128a, 128b abut each other, the recesses 132a, 132b face each other and form a single annular recess that is large enough to accommodate a ring seal, such as an O-ring seal for O-ring 134. The interior corner of wall 128b has a chamfer 130. Adjacent each recess 132a, 132b, and located away from the respective wall 128a, 128b, is a tapered recess 135a, 135b. Each tapered recess has a trapezoidal cross-section.

When the ends 128a, 128b abut each other, a V-band clamp 136 engages the recesses 135 to hold the parts 122a, 122b together. The V-Band clamp has two semi-circular or clamshell segments 136a, 136b, each of which has two projections 140a, 140b with tapered sides configured to mate with one of the recesses 135a, 135b. The clamshells segments 136a, 136b are fastened together, for example by threaded fasteners 142 such as screws, with the projections 140a, 140b wedging into the mating recesses 134a, 134b to fasten the segments 122a, 122b together. The seal 134 maintains a fluid tight seal alone, or in cooperation with the V-band clamp 136. The V-band clamp 136 also maintains the slurry chamber 122a and column 122b in coaxial alignment.

The removable slurry chamber 122a has an upstream end 124 with a chamfer 86 on the inside of the lip on the end of the chamber.

Referring to FIGS. 9a, 9b and 11, when assembled the initial use is similar to that of the first embodiment of FIG. 5. The slurry chamber 122a and column 122b are joined by a V-band 136. The downstream end cap 24 is placed on column 122b to hold the downstream frit 30 in place. The joined slurry chamber 122a and column 122b are placed in a holder with the upstream end of the upstream tube 122a being open rather than covered. Preferably, but optionally, the joined chamber 122a and column 122b are placed in a chuck 87 (FIG. 5) or a recess 174 in support 88 which holds the joined columns so the centerline 52 aligns with the centerline of the chuck. The downstream end of cap 24 can abut a support surface 88 as shown, or if the chuck 87 alone is used it can grip the joined bodies 122a, 122b sufficiently for the following packing. It is preferably to abut the column against support 88.

A predetermined amount of media 44 is placed in a beaker and mixed with a fluid to form a slurry. The slurry is preferably sonicated to remove air and further mix the media 44 and fluid. The slurry is then poured into the opening of the slurry chamber 122a. The slurry chamber 122a serves the purpose of a removable, pre-compression chamber in this second embodiment. The flask is rinsed with the fluid, preferably twice, and the fluid poured into the slurry chamber 122a in order to ensure all the media is placed into the joined bodies 122a, 122b. Additional fluid is added, if needed to fill the fluid level to the chamfer 86 on the slurry chamber 122a. It is undesirable to force air through the column, so the fluid level is high enough to avoid air entrapment or a release valve is provided. The outlet passage 26 is preferably not blocked at this stage so fluid can exit through the outlet 26 under the force of gravity.

Figure 18:
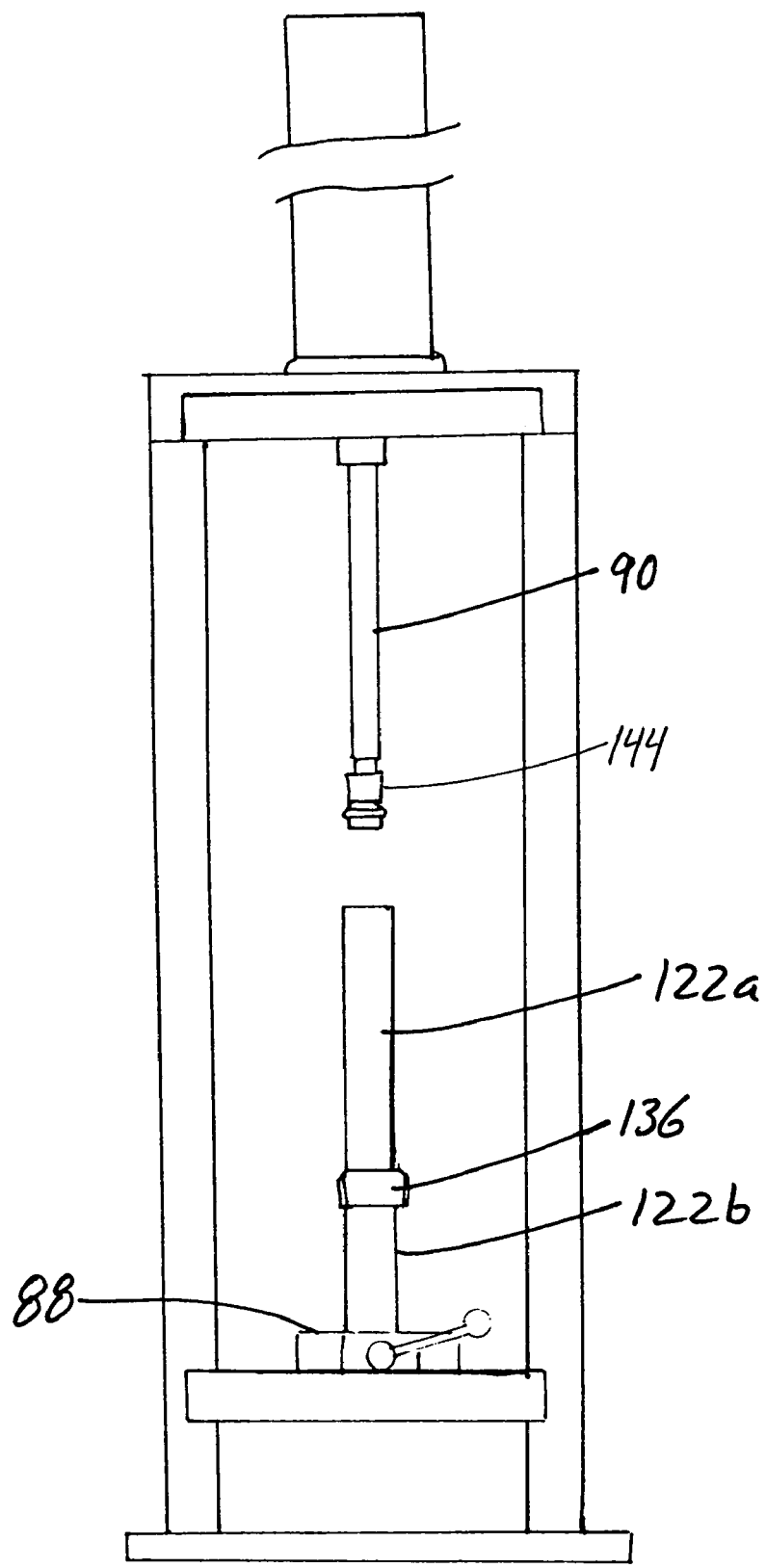
FIG. 18 is a side plan view of a press holding the assembly of FIG. 9a before the media is packed.

The piston 40 is placed onto the piston sleeve 46 so the end of the sleeve abuts the shoulder 69 on piston 40. Preferably mating threads on boss 70 engage mating threads on the inside of sleeve 46 to form a threaded engagement that prevents relative axial movement of the sleeve and piston. Advantageously a metal cap is placed over the end of sleeve 46 to block fluid flow out of the upstream end 78a of tube 78. The hat-shaped frit 42 is placed in the piston, and the upstream end cap 48 and thrust washer 50 are placed on the piston sleeve 46. As desired, a locking mechanism is placed on the sleeve 46. The piston sleeve 46 placed into a press 90 (FIG. 18). The detent 82 can engage a mating releasable detent pin in the press 90 to hold the piston sleeve 46 in place, along with any locking mechanism and piston 40 connected to the sleeve 46. The piston sleeve 46 is positioned in the ram 90 such that the longitudinal axis of the sleeve coincides with the longitudinal axis 52 of the body 22.

The ram 90 (FIGS. 5 and 18) then advances the piston into open end of the body 122a, with the chamfer 86 helping to guide the mating parts and accommodate slight misalignments. The advancement of the ram 90 and piston 40 is slow during this initial engagement portion. Preferably the movement of the piston 40 is paused before the first seal 60 engages the body 122a in order to verify alignment. Preferably a slight amount of excess fluid is forced over the chamfered lip 86 in order to ensure no air is entrapped between the frit 42 and the fluid.

The ram 90 advances the piston 40 into the joined bodies 122a, 122b. The pressure increases linearly, and slowly while the piston 40 is in the upstream slurry chamber 122a because there is enough fluid that the media 44 has not yet been compacted into a stationary bed. The tubular chamber 122a thus effectively forms a pre-compression chamber. The chamfer 130 on wall 128b at the juncture of the bodies 122a, 122b helps avoid the catching the seals 60, 62 and sealing wear ring 66. The chamfer 130 is preferably small, because media 44 can collect in the chamfer.

The advancing piston 40 forces fluid out the outlet passage 26 while the frit 30 retains the media inside the downstream body 122b. When the fluid is largely expelled from the downstream column 122b the piston 40 begins to compress the media 44 at which point the pressure rapidly increases as indicated by FIG. 6.

The ram 90 advances the piston 40 until a desired pressure is reached at which point movement of the piston 40 is halted and maintained in position. At that point the fluid is largely pressed out through passage 26 and the media 44 is compacted to form a bed of stationary phase for a desired use, preferably for chromatographic analysis. At this point the packed tube could be used for chromatographic analysis, but the ram 90 would have to maintain the pressure, and that is undesirable as it restricts mobility of the packed column 122b and restricts use of ram 90.

The length of the downstream column 122b is selected so that the media 44 and preferably, but optionally, at least a portion of the piston 40 is in the column 122b. Advantageously the seals 60 and 62 engage the wall 38 of the column 122, and preferably the wear ring 66 also engages the wall of the column, so a substantial portion of the piston is in the column 122b. The V-band 136 is then released so the removable slurry chamber 122a can be moved out of contact with the column 122b, while the piston is fastened to the column 122b and while the pressure on the media 44 is maintained by sleeve 46 and ram 90. The pre-compression chamber formed by slurry chamber 122a is thus removable and does not form a portion of the final assembled column 20 in this embodiment.

Figure 10:
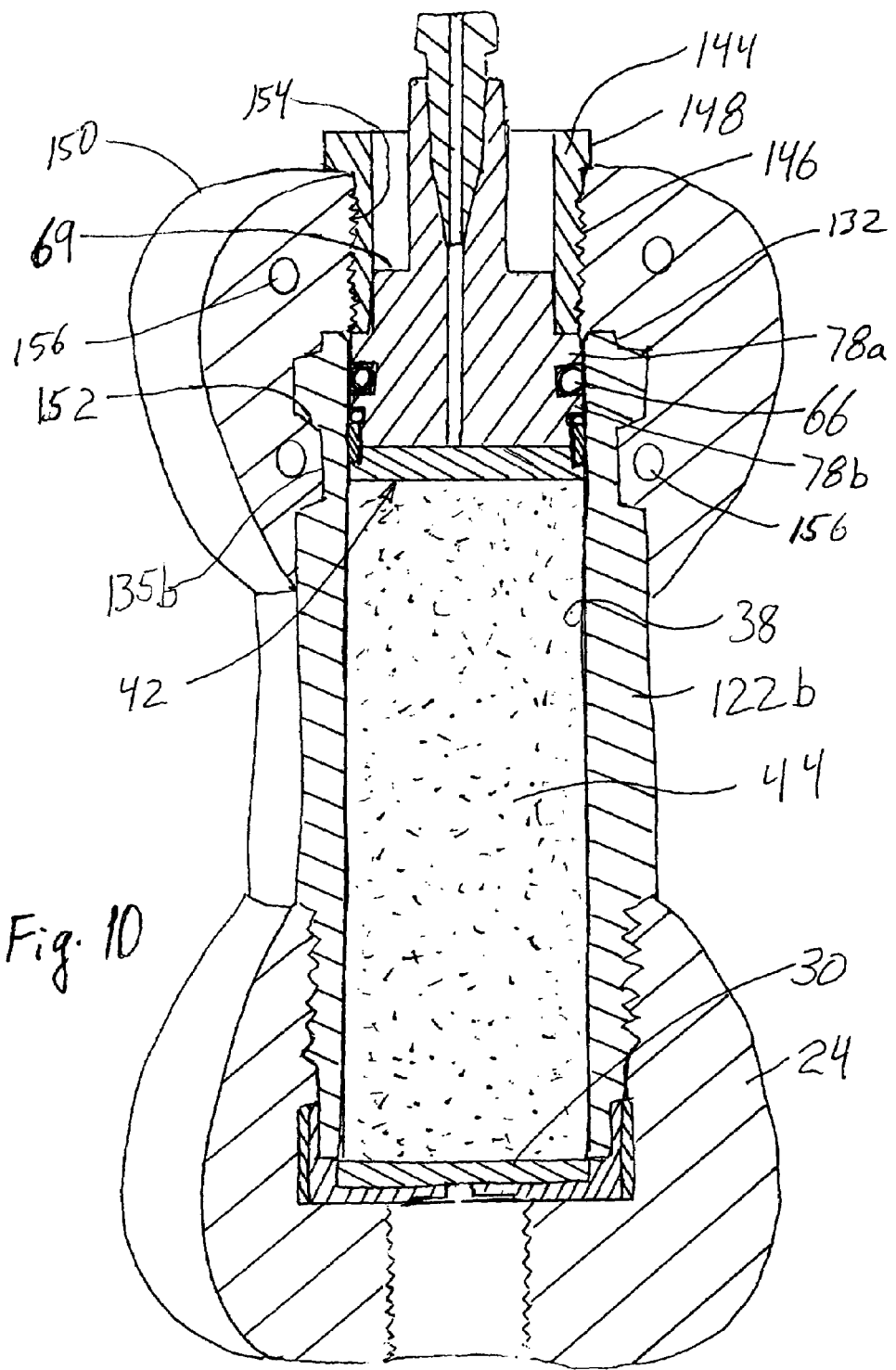
FIG. 10 is a sectional view of a column of FIG. 8 packed with media and held by a piston locked in position.

The piston 40 can be fastened to the column 122b various ways. Conceptually the preferred mechanisms involve clamshell or split-ring devices which engage a flange or recess on the column 122b and also engage part of the piston 40 in order to prevent relative movement of the piston 40 relative to the column 122b. One way locking the piston in place relative to column 122b is shown in FIG. 10. The piston 40 is pressed at least part way into the column 122b, preferably with the wear ring 66 and ridges 68a, 68b abutting the inner wall 38 of the column 122b. A locking collet 144 is placed around a portion of the piston 40, preferably abutting the upstream ridge 78a. The collet 144 acts as a piston compression screw. Advantageously, but optionally, the exterior of the collet 144 has a threaded portion 146 and a wrenching surface 144 is also provided, preferably on the upstream end of the collet. The collet 144 thus advantageously comprises a cylindrical tube having threads on an outer surface, with the tube being split—preferably along a longitudinal axis of the column 122b. A two-piece locking sleeve 150 then encloses a portion of the locking collet 144 and the column 122b. The locking sleeve 150 serves as a piston retainer and may be referred to as such. Preferably, but optionally, the locking sleeve 150 is a clamshell or split-ring configuration having a protrusion 152 configured to mate with recess 135b in the column 122b. Optionally, the locking sleeve 150 is preferably configured to mate with the exterior profile of upstream end of column 122b. Further, the locking sleeve 150 optionally has a threaded portion 154 located to threadingly engage threads 146 on collet 144. The threads 146, 154 are preferably, but optionally, multiple lead threads, with double lead threads being preferred. The collet 144 can be threaded into the recess 154 before or after the split locking sleeve 150 is joined together.

In use, after the upstream slurry tube or slurry chamber 122a is removed by sliding it up the piston sleeve 46. The two halves of the locking sleeve 150 are then fastened together, as for example, by threaded fasteners such as screws through holes 156 in the locking sleeve 150. Alternatively, a hoop fastener encircling the exterior of the sleeve 150 could be used, such as a hose clamp, a wire, a ring, or a cylinder could be used.

After the two parts forming locking sleeve 150 are joined, the collet 144 is then threadingly advanced or tightened in the sleeve 150 until the downstream end of collet 144 pushes against the ridge 78a on piston 40, and slightly increases the force detected by ram 90. The ram is then removed from engagement with shoulder 69, with the collet 144 and locking sleeve 150 maintaining substantially the same preload as provided by the ram 90. The packed column 122b is then removed from the chuck 87 ore recess 174, the downstream end plugged with plug 28 (FIG. 1), and the metal cap on the upstream end is replaced, as desired.

The collet 144 provides an axially positionable or adjustable device that accommodates variation in the position of the piston 40 along longitudinal axis 52. The collet 144 is preferably a unitary piece, or it can optionally be split into two or more pieces. The split locking sleeve 150 provides a radially locking device that engages the collet radially relative to axis 52, to prevent movement of the collet 144 along the longitudinal axis 52. By providing a collet 144 and multi-part locking sleeve 150, the ram 90 and piston sleeve 46 can maintain compressive pressure on the media 44 while the force needed to maintain that pressure is mechanically transferred to the locking sleeve 150 and column 122b without substantially releasing the pressure. While a single piece collet 144 and two-piece sleeve 150 are described, more than two parts could be used for each or the collet could be two-parts.

The wrenching surface 148 on the collet 144 is shown as being located on a flange that extends radially outward from axis 52 a distance greater than the inner diameter of wall 38 of column 122b. If the wrenching surface 148 is slightly smaller than the diameter of inner wall 38 of the column 122b, then the collet 144 could fit through the inside of the upstream slurry chamber 122a. Thus, it is believed possible that a single-piece collet 144 could be placed on the sleeve 46 and pass through the upstream tube or chamber 122a to be fastened to the locking sleeve 150 after the V-band clamp 136 is released.

Figure 12:
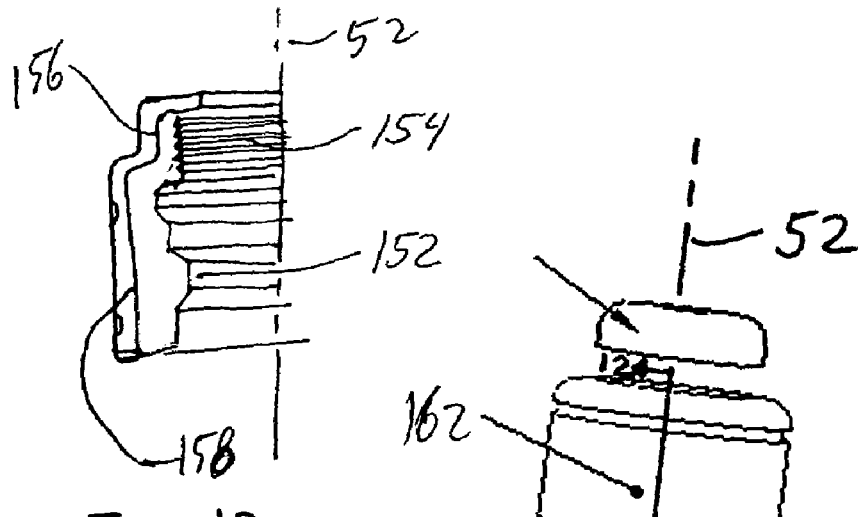
FIG. 12 is sectional view taken along 12-12 of FIG. 13.
Figure 13:
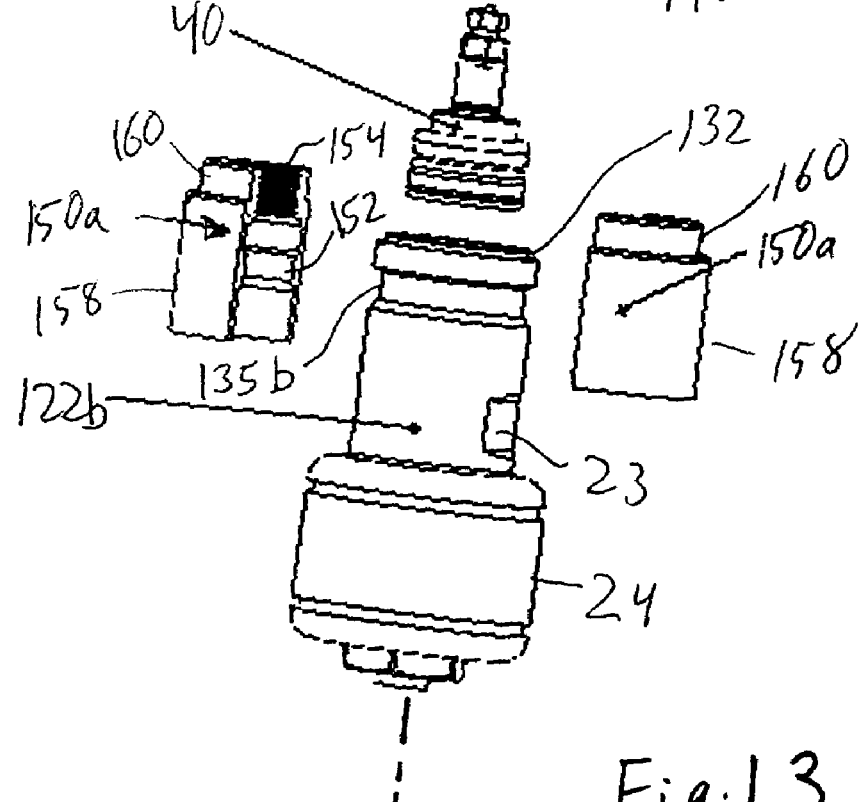
FIG. 13 is an exploded perspective view of a further embodiment of a locking mechanism for the column of FIG. 10.

Referring to FIGS. 12-13, an alternative locking mechanism is shown. The column 122b has a downstream end cap 24 and a body wrenching surface 23 and an upstream end as described above with recess 135b for receiving a part of the V-band clamp 136. Piston 40 is shown, along with collet 144 which acts as a compression screw. In this embodiment the locking sleeve 150a has an interior configured to conform to at least a portion of the exterior of the upstream end of column 122b, and preferably with a protrusion 152 configured to engage at least the recess 135b in the column 122b. The end 150a also has a threaded portion 154 configured to engage threads 146 on the collet 144.

The exterior of each of the two locking sleeves 150a has a substantially cylindrical lower portion 158 and a smaller sized cylindrical upper portion 160. The two halves 150a are fitted to engage the piston 40 and upstream end of column 122b. A holding piece 162 is then slipped over the outside of the two pieces 150a to prevent them from moving radially outward. The holding piece 162 has an interior profile shaped to mate with the exterior profile of pieces 150a. The holding piece 162 has downstream end that is large enough to pass over the outside of the lower portion 158, and has an upstream end large enough to pass over slurry chamber 122*a*. The interior of holding piece 162 nests over the exterior of locking sleeve 150*a*.

As the collet 144 is screwed into the threads 154 and is forced against the shoulder on ridge 78*a*, the pieces 150*a* will move radially outward away from axis 52 so they push against the inside of holding piece 156. Outward movement of the split ends 150*a* will wedge against the holding piece so that frictional engagement between the locking sleeves 150*a* and holding piece 162 will restrain axial movement of parts 150*a*, 162, with the shoulder formed by the different diameters of the upper and lower portions 158, 160 also restraining axial movement in one direction. The holding piece 158 can be placed over the piston sleeve 46 before the ram 90 pushes the piston 40 into the upstream slurry chamber 122*a*. After the chamber 122*a* is disengaged, the holding piece 156 passes over the chamber 122*a* to be fit over the end pieces 150*a* and hold them in place.

Referring to FIGS. 14*a* and 14*b*, a further embodiment is shown. This embodiment is as generally described above, but has a two or more piece segmented locking or retaining sleeve 150 surrounding the compression screw or collet 144. The holding piece 162 is also segmented, preferably with two segments. The segments enclose the collet 144 and the top end 124 of the column 122*b* to hold them in relative position. The segments of the holding piece 162 are fastened together by screws, bolts or pins 142.

This construction eliminates the need to have the sleeve 46 (FIG. 5) remain with the packed column 20, and it eliminates the need for a tube long enough to accommodate the length of sleeve 46. The resulting column 20 is shorter, lighter, and simpler, uses less hardware, and is less expensive. Moreover, the dynamic, hydraulic packing of media 44 is more accurate and repeatable, the stationary phase is more uniformly formed, and the bed density is increased—while avoiding crushing the bed and creating fines. The column performance is improved.

Further, the hydraulic packing of media 44 takes significantly less time to achieve than conventional packing methods which continuously run slurry through the tube to pack the tube, by a factor of about 10 to 100 times faster. The tubes 22, 122 can be packed to the desired pressure in less than a minute for tube diameters of an inch or less and lengths of a few inches or less.

Moreover, less media 44 is used, and the media is expensive. The prior continuous flow (slurry) packing technique can have up to about 40% of the media remaining in the tube or chamber used with the packing equipment.

Still further, the dynamic, hydraulic packing by piston 40 compresses the media 44 to form a stationary bed of compressed media, and that compressed bed of media is locked into position without being allowed to relax or expand. The locking of the bed into the desired compression is achieved in the first embodiment by locking the piston sleeve 46 into position in order to hold the piston 40 in position. In the second embodiment the piston 40 is locked into position and then the piston sleeve 46 is removed. In both embodiments the pressure exerted by piston 40 on the bed of media 44 is preferably maintained substantially unchanged. Actually because the locking mechanism in both instances preferably is actuated until a piston movement or slight pressure increase is detected by the ram 90, the locking pressure is preferably slightly higher, preferably within a fraction of a psi higher, and less preferably within a few psi or tens of psi higher than of the packing pressure at which the ram 90 stops moving. Because the pressure on piston 40 is electronically monitored by the ram 90 (e.g., through strain gauges, pressure transducers, etc.), it is possible, but not preferable, to lock the piston 40 at a pressure greater than or less than the pressure at which the ram 90 initially stops the compression.

Advantageously, no springs are interposed between the piston and the locking end 48 and locking sleeve 150 which hold the piston 40 and bed of packed media 44 in compression.

The frits 30, 42 are made of sintered metal, or polymerized PEEK. The two-diameter frit 42 allows fluid distribution across the entire stationary phase provided by the packed media 44. The outer diameter of frit 42 is smaller than the inner diameter of wall 38 to avoid scratching the wall as the frit 42 is moved by press 90 and piston 40 along the wall. The hat shaped frit 42 allows the frit to extend across substantially all the interior diameter of the tube 22, 122*b*, and to extend across the entire stationary bed formed from media 44. That provides more uniform distribution of the mobile phase and sample over the media 44, and that is especially useful when the columns 20 are short. Further, the boss 58 allows a substantial portion of the frit, about 70-80% to be thickened to better withstand packing pressures, and provides a thinner peripheral rim of thinner material. The frit 42 is preferably a unitary frit formed into the hat-shaped structure at the time of manufacture. Alternatively, but less preferably, the frit 42 can be formed from placing a larger diameter frit abutting a narrower diameter frit. A stainless steel frit 47 having a boss 58 of about 3.5 mm axial thickness, with a flange 56 having about 1.3 mm axial thickness, for a flange diameter of about 21 mm and a boss diameter of about 18 mm, is believed suitable for a porosity of about 2 microns. The frit allows passage of a fluid containing substances in solution to be separated while not allowing solid particles in the chromatographic medium to pass. Ideally, radial grooves inside the frit or on an upstream surface of the frit allow the solution to spread more evenly across the surface of the fit to help more evenly spread the fluid across the bed of chromatographic media 44.

The stepped-diameter frit 42 can be made by taking a disk having the desired maximum thickness and diameter, and then turning the smaller diameter boss 58. This part can also be molded or sintered of metal, and possibly of ceramic. Preferably the upstream side of the boss 58 and the downstream facing side of the flange 56 are porous, with the edges and the annular space between boss 58 and the periphery of the larger flange 56 being substantially impervious to fluid flow.

The seal 60, and any additional seals, are sufficiently fluid tight to sweep any media along the length of the chambers 22, 122*a*, 122*b*. The seal 60, and any optional further seals are configured for the desired packing and operating pressures which typically range from 1,000-6,000 psi to 10,000 psi and possibly higher. While specific seal configurations are shown, other seal configurations, seal arrangements, and seal materials can be used within the spirit and scope of the present invention.

The seal between the ends of chamber 122*a* and tube 122*b* can be simplified greatly if the downstream tube 122*b* is sized so the maximum pressure increase occurs after the seal 60 or seals 60, 62 and 66 have passed the chamfered 130 on the tube 122*b*. That simplifies the construction, assembly and disassembly of the chamber 122*a* and tube 122*b*. The chamfer 130 is preferably formed only on the downstream tube 122*b* in order to avoid forcing media into the joint between chamber 122*a* and tube 122*b* as the piston passes the chamfer 130.

Referring to FIGS. 9*a* and 9*b*, a further embodiment is shown. An upstream tube or chamber 122*a* is joined to a downstream tube or column 122*b* by a split retainer. The top or upstream end 124 of the column 122b has a top end recess 135b and the bottom or downstream end of the upstream tube or chamber 122a has a bottom end recess 135a. A threaded collet or bed compression screw 144 threadingly engages mating threads on the inside of the upstream end of the column 122b. The piston 40 (FIG. 13) is urged against the media bed by the compression screw 144.

The locking sleeve 150 (FIG. 13 or FIG. 10) has a threaded upstream end to mate with the exterior threads on bed compression screw 144 or collet 144. The sleeve 150 has a downstream end configured to engage the recess 135b, or the rim forming the recess 135b, to restrain axial movement of the sleeve 150. The sleeve 150 thus restrains movement of the collet 144 relative to the column 122b along the longitudinal axis 52. An outer sleeve or holding piece 162 holds the split sleeve 150 from radial expansion. The outer sleeve 162 is also a split or clamshell design with the two or more pieces held together by threaded fasteners 142 extending through aligned holes in the mating parts of the outer sleeve 162. The interior of the outer sleeve 162 is configured to generally conform to the exterior of the split locking sleeve 150 or collet. The outer sleeve 162 holds the parts of the sleeve 150 together.

The initial use is as described above wherein a V-band clamp 136 holds the upstream slurry tube 122a and downstream column 122b in alignment during filling and packing as the piston 40 (not shown) compresses the media to form a chromatographic bed. The V-band clamp is removed.

Figure 14:
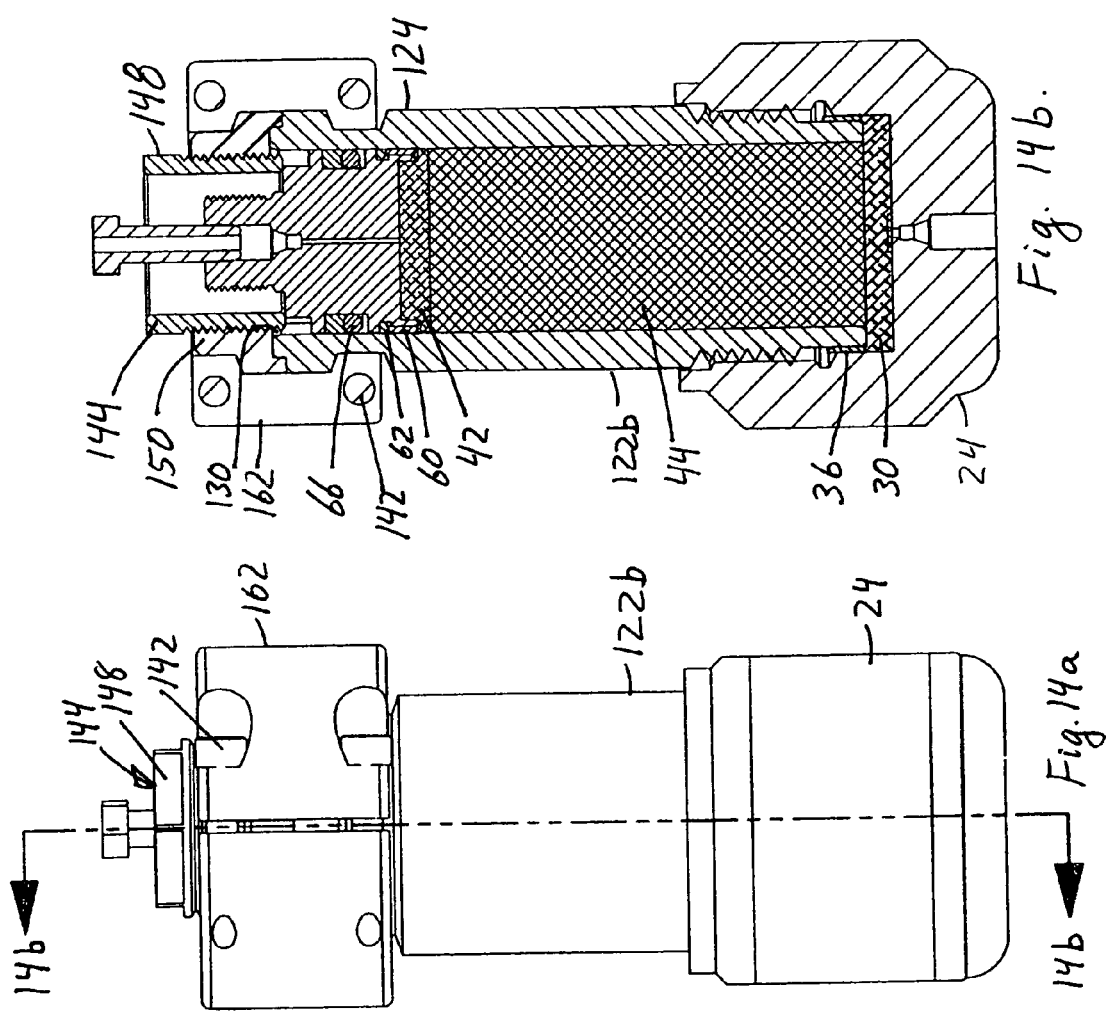

Referring to FIG. 14, the split collar 150 is then placed around the column 122b to engage the recess 135b. The split collar 150 serves to retain the piston in place and for ease of understanding the collar 150 will be referred to as a piston retainer in describing the operation of FIG. 14. The bed compression screw or sleeve 144 is then slid down so its threads engage the threads on the piston retainer 150. The bed compression screw or sleeve 144 is tightened until the piston is locked in place. As the bed compression screw is tightened it pushes in an upward or upstream direction against the piston retainer 150 and recess 135b. The inclined surfaces on the recess 135b allow the split piston retainer 150 to move outward from axis 52, and the outer sleeve 162 restrains that motion, locking everything in place. The packed column 122b can then be removed from the press 90, and flow through the column blocked by plugs 28 and cap 80.

Instead of using a split outer sleeve 162 and fasteners 142 to restrain outward expansion of the split piston retainer 150, the piston retainer could be held together and held in place by wire, by an encircling ring slid axially over the retainer 150, or by a cylindrical sleeve slid axially over the retainer 150. The use of single-piece rings or sleeves is simpler in that it avoids the use of split parts and fasteners to hold the split parts together. But the single piece rings or sleeves require they be positioned on the longitudinal axis 52 before bed compression begins, and that can complicate arranging all the parts on the axis while still accommodating compression by the press 90.

Figure 15:
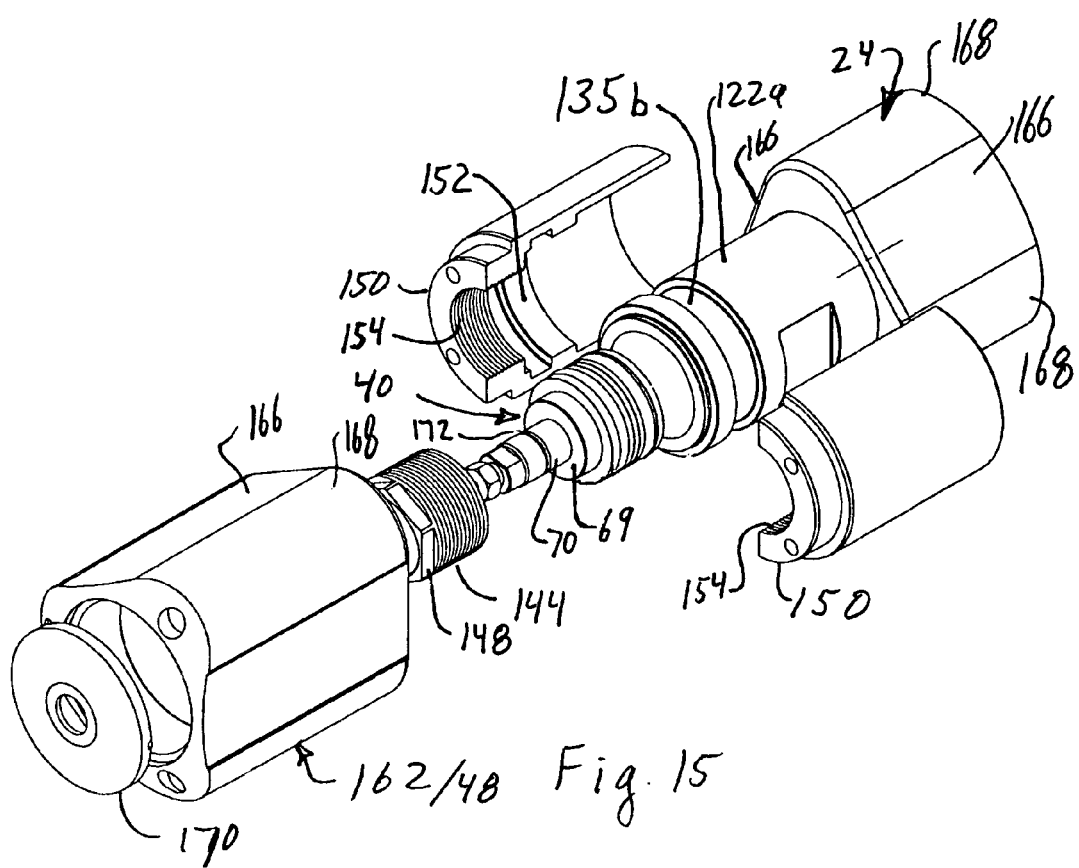
FIG. 15 is an exploded perspective view of a further embodiment for locking the piston to the column.

Referring to FIGS. 15-17, a further embodiment is shown. The downstream end cap 24 has a plurality of flat surfaces 166 and corners 168 that can be used to align the column 122a for packing with the press 90. Preferably, but optionally, the split locking sleeve 150 is elongated to extend along a substantial length of the column 122a, and for columns shorter than 50 mm a substantial length is about half or more. For longer columns the length is shorter and does not comprise a substantial length. The locking sleeve 150 has internal threads 154 configures to engage threads on the piston compression screw or collet 144. A protrusion 152 mates with recess 135b in the column 122a to prevent relative axial motion of the piston retaining sleeve 150 and the column 122a. The protrusion 152 is preferably shaped to conform with the shape of recess 135b and more preferably has inclined walls to wedge radially and form a tight fit that restrains axial motion. The locking sleeve 150 preferably conforms to the distal end of the column 122a to provide further engaging surfaces that restrain relative axial movement between the sleeve 150 and column 122a. The locking sleeve 150 has a cylindrical exterior along its length, with a reduced diameter adjacent the threads 154.

The upstream end cap 48 preferably, but optionally, has similar flats 166 and corners 168 as does the downstream end cap 24. The upstream end cap 48 forms the holding piece 162 to confine radial expansion of the split locking sleeve 150. This is achieved by having an interior recess configured to conform to the exterior of the locking sleeve 150, or to conform to substantial portions of that exterior. As illustrated, a number of mating protrusions and recesses can be used to provide resistance to axial movement of the locking sleeve 150 relative to the column 122a.

When the parts of the locking sleeve 150 are positioned to engage the column 122a, the holding portion 162 is moved axially to fit over the locking sleeve 150 and prevent radial expansion. As the collet 144 engages threads 154 and is tightened to abut piston 40, the tightening of the mating threads will cause radial motion of the locking sleeve 150, which abuts the holding piece 162 to frictionally lock the parts together.

Upon suitable tightening of the collet 144, the press 90 is disengaged and the column 122a removed. An end cover 170 can optionally be placed over a larger diameter recess in the holding piece 162 (that forms the end cap 48). The larger diameter recess allows easier access to the wrenching surface 148 on the collet 144. As desired, suitable plugs or caps are added to block the fluid flow channels through the packed column 122a.

The flats 166 and/or corners 168 allow the column 122a to be placed in a recess 174 (FIG. 11) in support 88 where the recess is configured to conform to the flats and/or corners, in order to align the longitudinal axis of the column 122a with the longitudinal axis of the press 90. That avoids the need for a chuck 87. Any suitable number of flats and/or corners can be used as long as a suitable alignment is achieved.

The embodiment of FIGS. 15-17 also has a modified piston 40 as shown in FIGS. 3a and 3b. The boss 70 has no threads, and instead has a detent groove 172 which mates with a detent pin or detent ring (not shown) in the piston sleeve 46 to releasably hold the piston in the press during use. The detent ring and groove 172 are easier to use than mating threads on the piston sleeve 46 and boss 70 as shown in FIGS. 1 and 3a.

As used herein, the terms upstream and downstream are relative to an initial packing orientation for the columns 20, 122. The relative directions can be referred to as first and second, and the directions themselves can be reversed, and the parts referred to can also be reversed. The frits 30, 42 are formed of sintered metal (stainless steel, titanium or other suitable porous material).

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

The above description is given by way of example, and not limitation. Given the above disclosure, one skilled in the art could devise variations that are within the scope and spirit of the invention, including various ways of locking the piston in place inside the column 20 and various ways to releasably join the slurry chamber 122a to the column 122b. Further, the various features of this invention can be used alone, or in varying combinations with each other and are not intended to be limited to the specific combination described herein. Thus, the invention is not to be limited by the illustrated embodiments.

What is claimed is:

1. A method for packing a compact, disposable, tubular chromatographic column having a first and second opposing ends defining a first length and having an end cap on the first end of the column, the column having an interior diameter, comprising:
    aligning a slurry pre-compression chamber to the second end of the column and coaxially with the column;
    forming a fluid tight seal between the slurry pre-compression chamber and the second end of the column;
    placing a slurry of fluid and chromatographic media in the column- and slurry pre-compression chamber;
    placing a piston in the slurry pre-compression chamber, the piston having seals interposed between the piston and the slurry pre-compression chamber and a frit interposed between the piston and the slurry;
    advancing the piston through the slurry pre-compression chamber and at least part way into the column such that the piston exerts pressure on the chromatography media placed in the column;
    stopping the advancement of the piston when the media in the slurry forms a bed that is compacted to a desired pressure in the column; and
    removing the slurry pre-compression chamber from the column while substantially maintaining with the piston said desired pressure on the chromatography media placed in the column, and locking the piston in place with a piston retainer while substantially maintaining the pressure.

2. The method of claim 1, further comprising:
    locking the piston to the column without releasing the pressure on the bed.

3. The method of claim 2, wherein the locking step includes placing a V-band clamp around the second end of the column.

4. The method of claim 1, further comprising:
    locking the piston to the column while slightly releasing the pressure on the bed.

5. The method of claim 1, wherein a seal is interposed between a smaller diameter and the interior diameter of the column and no seal is interposed between a larger diameter and the interior diameter of the column.

6. The method of claim 1, wherein the disengaging step includes separating the slurry pre-compression chamber from the column.

7. The method of claim 6 wherein the disengaging step further comprises the steps of:
    placing an end cap over the second end of the column, the end cap having threads;
    placing a collet in threaded engagement with the threads of the end cap; and
    advancing the collet toward the piston within the column until the piston exerts the desired pressure on the chromatography media placed in the column.

8. The method of claim 7 wherein the locking step comprises placing two parts of a split, annular locking sleeve around the collet and a portion of column to restrain movement between the collet and the column along a longitudinally axis of the column, and restraining radial expansion of the locking sleeve.

9. The method of claim 7 wherein the placing the collet step comprises the step of traversing the collet out of the slurry pre-compression chamber and into engagement with the threads of the end cap.

10. The method of claim 1, wherein advancing the piston comprises placing a hydraulic ram in contact with a shoulder on the piston and advancing the hydraulic ram.

11. The method of claim 10,
    wherein the ram position is maintained until the slurry pre-compression chamber is removed from contact with the column and until the piston is locked in place.

12. The method of claim 11, further comprising removing the column from the ram, and plugging an outlet in the first end of the column.

13. The method of claim 1, wherein forming the fluid tight seal includes placing a V-band clamp over the juncture of the slurry pre-compression chamber and the column.

14. The method of claim 1, wherein the forming step comprises the steps of inserting an o-ring between the second end of the column and the slurry pre-compression chamber and compressing the o-ring therebetween.

15. The method of claim 1 wherein the forming step comprises the steps of forming a channel between the second end of the column and the slurry pre-compression chamber.

16. The method of claim 1 wherein the advancing step comprises the step of traversing the piston past a chamfer formed on an inner edge of the second end of the column.

17. The method of claim 1 further comprising locking the piston to the column while maintaining at least a minimum amount of pressure on the bed.

* * * * *